US012721604B2

(12) United States Patent
Shiran et al.

(10) Patent No.: US 12,721,604 B2
(45) Date of Patent: Sep. 1, 2026

(54) METHODS AND SYSTEMS FOR 3D TOPOGRAPHIC PLEURAL DISPLAY

(71) Applicant: GE Precision Healthcare LLC, Waukesha, WI (US)

(72) Inventors: Carmit Shiran, Middleton, WI (US); Menachem Halmann, Monona, WI (US); Doron Shaked, Haifa (IL); Ella Sokulin, Kiryat Tivon (IL); Alexander Sokulin, Kiryat Tivon (IL); Shreya Bhise, Milwaukee, WI (US); Or Elezra, Haifa (IL); Roei Gelbhart, Tel-Aviv (IL)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 76 days.

(21) Appl. No.: 18/979,426

(22) Filed: Dec. 12, 2024

(65) Prior Publication Data

US 2026/0165683 A1 Jun. 18, 2026

(51) Int. Cl.

| | |
|---|---|
| ***A61B 8/00*** | (2006.01) |
| ***A61B 8/08*** | (2006.01) |
| ***G06T 5/00*** | (2006.01) |
| ***G06T 7/00*** | (2017.01) |

(52) U.S. Cl.

CPC ............ *A61B 8/5215* (2013.01); *A61B 8/085* (2013.01); *A61B 8/463* (2013.01); *A61B 8/466* (2013.01); *G06T 5/00* (2013.01); *G06T 7/0012* (2013.01); *A61B 2576/02* (2013.01); *G06T 2200/04* (2013.01); *G06T 2207/10136* (2013.01); *G06T 2207/20172* (2013.01); *G06T 2207/30061* (2013.01)

(58) Field of Classification Search

CPC .................................................... A61B 8/5215

See application file for complete search history.

(56) References Cited

U.S. PATENT DOCUMENTS

| | | | |
|---|---|---|---|
| 9,119,670 | B2 | 9/2015 | Yang et al. |
| 10,650,512 | B2 | 5/2020 | Hoff et al. |
| 10,667,793 | B2 | 6/2020 | Halmann et al. |
| 10,758,206 | B2 | 9/2020 | Halmann et al. |
| 11,227,392 | B2 | 1/2022 | Halmann |

(Continued)

OTHER PUBLICATIONS

Correa, M. et al., "Automatic classification of pediatric pneumonia based on lung ultrasound pattern recognition," PloS One, vol. 13, No. 12, Dec. 5, 2018, 13 pages.

(Continued)

*Primary Examiner* — Joseph M Santos Rodriguez
(74) *Attorney, Agent, or Firm* — McCoy Russell LLP

(57) ABSTRACT

Various methods and systems are provided for a medical imaging system. In one embodiment, a method for imaging a lung of a patient includes identifying, within a three-dimensional (3D) volume of ultrasound data of the lung of the patient, a pleural surface of a pleural line, identifying an orthogonal deviation of each voxel of the pleural surface relative to an expected pleural line, and outputting an image rendered from the 3D volume, the image including a plurality of pixels colored based on the orthogonal deviation of each voxel of the pleural surface and depicting the pleural surface as if viewed from an inside of the lung and looking outward.

20 Claims, 10 Drawing Sheets
(4 of 10 Drawing Sheet(s) Filed in Color)

(56) References Cited

U.S. PATENT DOCUMENTS

| | | | | |
|---|---|---|---|---|
| 11,446,008 | B2 | 9/2022 | Mehanian et al. | |
| 11,627,941 | B2 | 4/2023 | Halmann et al. | |
| 2019/0105013 | A1* | 4/2019 | Wang | A61B 8/463 |
| 2019/0336108 | A1* | 11/2019 | Hope Simpson | G06T 7/0012 |
| 2021/0295800 | A1* | 9/2021 | Muijs | G06T 5/50 |
| 2022/0061813 | A1* | 3/2022 | Halmann | A61B 8/5253 |

OTHER PUBLICATIONS

Carrer, L. et al., "Automatic Pleural Line Extraction and COVID-19 Scoring From Lung Ultrasound Data," IEEE Transactions on Ultrasonics, Ferroelectrics, and Frequency Control, vol. 67, No. 11, Jun. 29, 2020, 11 pages.

Ebadi, S. et al., "Automated detection of pneumonia in lung ultrasound using deep video classification for COVID-19," Informatics in Medicine Unlocked, vol. 25, 2021, 9 pages.

Camacho, J. et al., "Artificial Intelligence and Democratization of the Use of Lung Ultrasound in COVID-19: On the Feasibility of Automatic Calculation of Lung Ultrasound Score," International Journal of Translational Medicine, vol. 2, No. 1, Jan. 13, 2022, 9 pages.

* cited by examiner

METHODS AND SYSTEMS FOR 3D TOPOGRAPHIC PLEURAL DISPLAY

STATEMENT REGARDING FEDERALLY SPONSORED RESEARCH AND DEVELOPMENT

This invention was made with government support under Grant No. 75A50123C00035 awarded by Biomedical Advanced Research and Development Authority (BARDA). The Government has certain rights in the invention.

FIELD

Embodiments of the subject matter disclosed herein relate to ultrasound imaging and, in particular, to visualizing a lung pleura as a topographic three-dimensional (3D) view.

BACKGROUND

An ultrasound imaging system typically includes an ultrasound probe that is applied to a patient's body and a workstation or device that is operably coupled to the probe. During a scan, the probe may be controlled by an operator of the system and is configured to transmit and receive ultrasound signals that are processed into an ultrasound image by the workstation or device. The workstation or device may show the ultrasound images as well as a plurality of user-selectable inputs through a display device. The operator or another user may interact with the workstation or device to analyze the images displayed on and/or selected from the plurality of user-selectable inputs.

As one example, ultrasound imaging may be used for examining a patient's lungs due to an ease of use of the ultrasound imaging system at a point-of-care and resource availability relative to a chest x-ray or a chest computed tomography (CT) scan, for example. Further, the ultrasound imaging system does not expose the patient to radiation. Lung ultrasound imaging, also termed lung sonography, includes interpreting a lung pleura for diagnostic purposes.

BRIEF DESCRIPTION

This summary introduces concepts that are described in more detail in the detailed description. It should not be used to identify essential features of the claimed subject matter, nor to limit the scope of the claimed subject matter.

In one aspect, a method for imaging a lung of a patient includes identifying, within a three-dimensional (3D) volume of ultrasound data of the lung of the patient, a pleural surface of a pleural line, identifying an orthogonal deviation of each voxel of the pleural surface relative to an expected pleural line, and outputting an image rendered from the 3D volume, the image including a plurality of pixels colored based on the orthogonal deviation of each voxel of the pleural surface and depicting the pleural surface as if viewed from an inside of the lung and looking outward.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will be better understood from reading the following description of non-limiting embodiments, with reference to the attached drawings, wherein below.

DETAILED DESCRIPTION

Embodiments of the present disclosure will now be described, by way of example, with reference to the FIGS. 1-10, which relate to various embodiments for visualizing a 3D representation of a pleural surface of a lung pleura viewed from an inside of a lung and looking outward. It is to be understood that, as described herein, a "3D pleural surface" is a 3D computer rendering which represents an anatomical region (e.g., a pleura) captured using an imaging system. In an aerated lung, the pleura, which form the outer boundary of the lung that lies against the chest wall, may provide the substantially only anatomical lung structure detectable by ultrasound. The pleura appear as a hyperechoic horizontal segment of brighter (e.g., whiter) pixels in a 2D ultrasound image, referred to as a pleural line, which moves synchronously with respiration in a phenomenon known as pleural sliding. The 3D pleural surface includes a volumetric topography of the lung pleura. Some topography of the pleura is shown in 2D ultrasound images; however, further detail of pleura topography may be visualized in a 3D pleural surface, which may help in identifying and/or diagnosing conditions of the lung that may be visualized as irregularities in pleural surface topography. Compared to what may be captured in a 2D ultrasound image, the 3D pleural surface may show pleural topography in a broader region of the lung. For example, the 3D pleural surface may be a live 3D surface rendering of the pleura, or may be a static image provided following data collection using the ultrasound probe. In some embodiments, the 3D pleural surface described herein may be a 4D image, where the 3D pleural surface is a 3D image which may change over time (e.g., in real-time) to reflect changes in patient anatomy visualized using the ultrasound probe (e.g., due to patient breathing, movement, etc.). The 3D pleural surface may be colored based on the relative depth of voxels within the 3D pleural surface in order to provide a topographic representation of the pleural surface.

Figure 1:
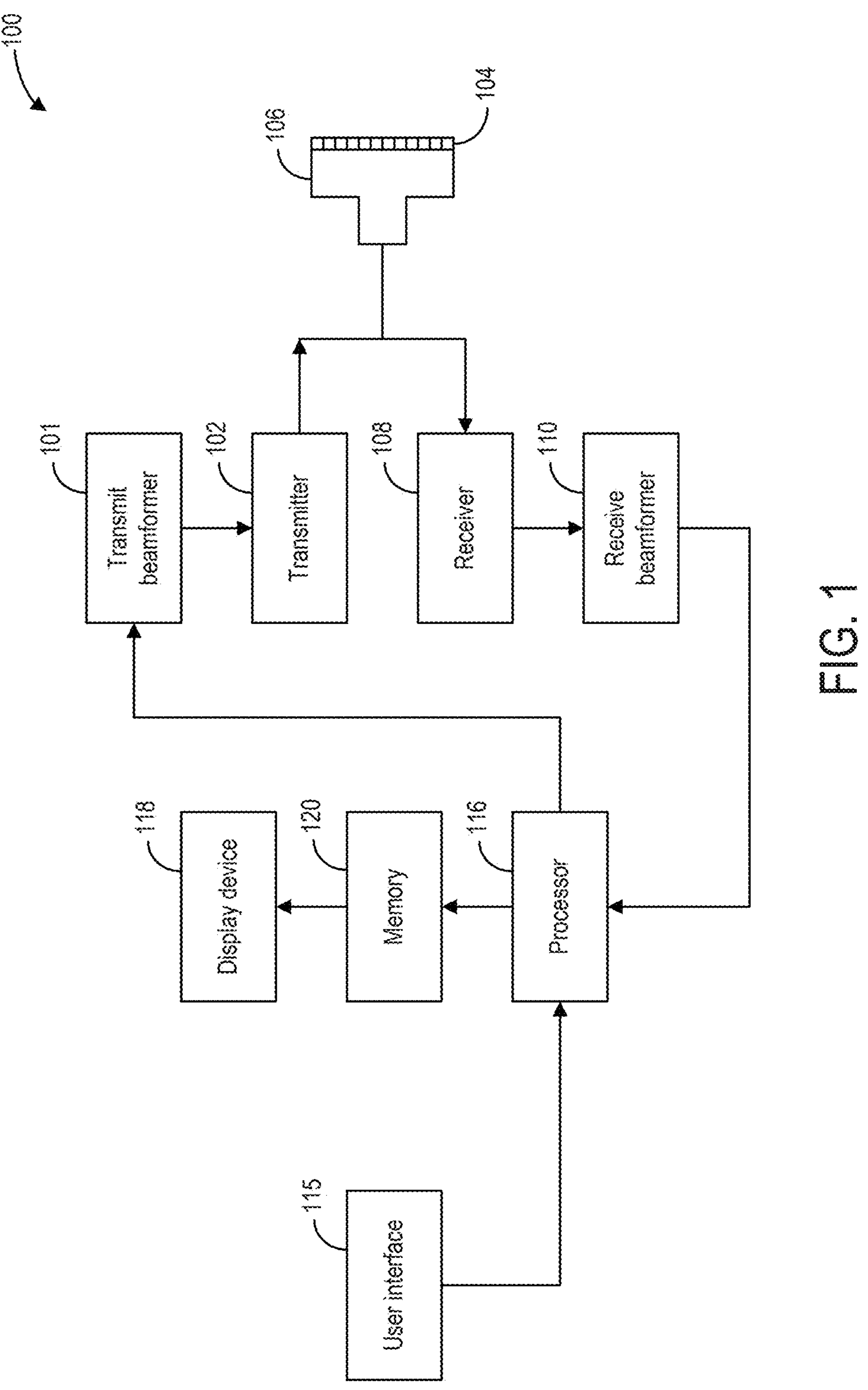
FIG. 1 shows a block schematic diagram of an ultrasound imaging system, according to an embodiment.
Figure 2:
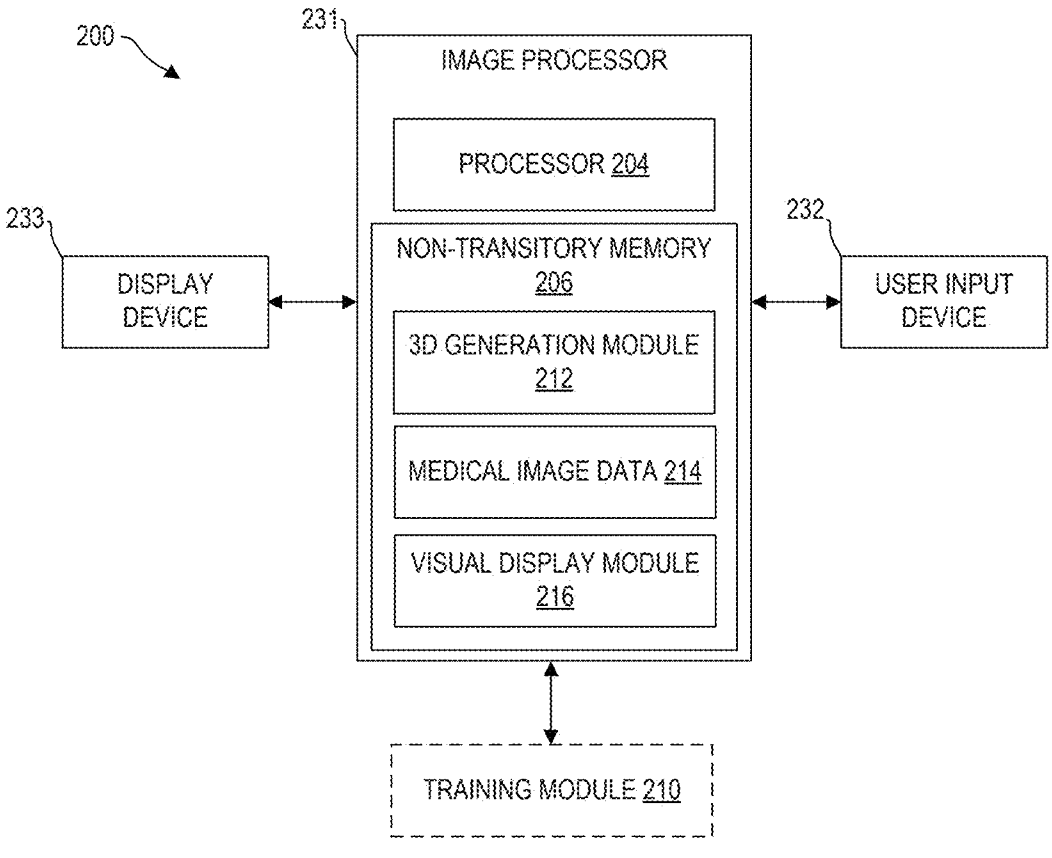
FIG. 2 is a schematic diagram illustrating an image processing system for generating topographic views of 3D pleural surfaces, according to embodiment.

The 3D pleural surface may be generated based on medical imaging data acquired by an imaging system, such as the ultrasound imaging system shown in FIG. 1. As the processes described herein may be applied to pre-processed imaging data and/or to processed images, the term "image" is generally used throughout the disclosure to denote both pre-processed and partially-processed image data (e.g., pre-beamformed RF or I/Q data, pre-scan converted RF data) as well as fully processed images (e.g., scan converted and filtered images ready for display). An example image processing system that may be used to generate the 3D pleural surface is shown in FIG. 2. The image processing system may employ image processing techniques and one or more algorithms to identify a pleural line in ultrasound imaging data and generate a 3D pleural surface viewed from an inside of a lung and looking outward. The 3D pleural surface may be generated from 3D ultrasound data, as described with respect to the method of FIG. 3 and visualized in FIG. 4. To aid in visualization, the 3D pleural surface may be colored based on depth to generate a topographic 3D pleural surface visualization according to the method of FIG. 5. FIG. 6 shows an example interface displaying the 3D pleural surface viewed from an inside of a lung and looking outward. FIGS. 7-10 show additional views of the interface displaying topographic 3D pleural surfaces, and optionally selected 2D slices and/or volumetric renderings of features of interest. In this way, pleural irregularities may be highlighted in a display of a 3D pleural surface generated from volumetric ultrasound imaging data in real-time, decreasing a time until a diagnosis can be made and decreasing both intra-operator and inter-operator variation.

Advantages that may be realized in the practice of some embodiments of the described systems and techniques are that inconsistencies in the detection of pleural irregularities, particularly between different operators, may be decreased. This may be particularly advantageous for increasing a detection accuracy of point-of-care ultrasound operators, who may have less training than ultrasound experts (e.g., sonographers or radiologists). For example, an emergency room physician, who may not receive expert-level ultrasound training, may be more likely to overlook an irregularity or incorrectly identify a normal structure or an imaging artifact as an irregularity, which may increase a burden on a radiology department for follow up scans and increase patient discomfort. Further, by decreasing follow up scans and a mental burden on the point-of-care ultrasound operator, an amount of time until an accurate diagnosis is made may be decreased. Although the systems and methods described below for evaluating medical images are discussed with reference to an ultrasound imaging system, it may be noted that the methods described herein may be applied to a plurality of imaging systems (e.g., MRI, PET, x-ray, CT, or other similar systems). Additionally, the topographic 3D pleural surface visualization described herein may include color coded topology where the color corresponds to the depth of the deviation of a topologic feature from the normal topology of the pleural surface. The color coding may make irregularities in the pleura easy to identify to clinicians. Clinicians may use the location, number, and depth of identified irregularities to form diagnoses. The topographic 3D pleural surface visualization may use fewer computing resources than computer-aided diagnosing programs, because the topographic 3D pleural surface enhances visualization of the depth of the topologic features in the pleura and does not undertake computationally-intensive operations that may be demanded to actually differentiate a pleural irregularity from a normal pleural surface.

Referring to FIG. 1, a schematic diagram of an ultrasound imaging system 100 in accordance with an embodiment of the disclosure is shown. However, it may be understood that embodiments set forth herein may be implemented using other types of medical imaging modalities (e.g., magnetic resonance imaging, computed tomography, positron emission tomography, and so on). The ultrasound imaging system 100 includes a transmit beamformer 101 and a transmitter 102 that drives transducer elements 104 within a transducer array, herein referred to as a probe 106, to emit pulsed ultrasonic signals (referred to herein as transmit pulses) into a body (not shown). According to an embodiment, the probe 106 may be a one-dimensional (1D) transducer array probe. In some embodiments, the probe 106 may be a two-dimensional (2D) matrix transducer array probe. In further embodiments, the probe 106 may be a 1.5-dimensional (1.5D) probe or any ultrasound probe capable of live 3D imaging, such as a matrix array probe. The transducer elements 104 may be comprised of a piezoelectric material. When a voltage is applied to the piezoelectric material, the piezoelectric material physically expands and contracts, emitting an ultrasonic spherical wave. In this way, the transducer elements 104 may convert electronic transmit signals into acoustic transmit beams.

After the transducer elements 104 of the probe 106 emit pulsed ultrasonic signals into a body (of a patient), the pulsed ultrasonic signals are back-scattered from structures within an interior of the body, like blood cells or muscular tissue, to produce echoes that return to the transducer elements 104. The echoes are converted into electrical signals, or ultrasound data, by the transducer elements 104, and the electrical signals are received by a receiver 108. The electrical signals representing the received echoes are passed through a receive beamformer 110 that performs beamforming and outputs ultrasound data, which may be in the form of a radiofrequency (RF) signal. Additionally, the transducer elements 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be positioned within the probe 106. The terms "scan" or "scanning" may also be used in this disclosure to refer to acquiring data through the process of transmitting and receiving ultrasonic signals. The term "data" may be used in this disclosure to refer to one or more datasets acquired with an ultrasound imaging system.

A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of a rotary element, a mouse, a keyboard, a trackball, hard keys linked to specific actions, soft keys that may be configured to control different functions, and a graphical user interface displayed on a display device 118. In some embodiments, the display device 118 may include a touch-sensitive display, and thus, the display device 118 may be included in the user interface 115.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. As used herein, the term "electronic communication" may be defined to include both wired and wireless communications. The processor 116 may control the probe 106 to acquire data according to instructions stored on a memory of the processor and/or a memory 120. As one example, the processor 116 controls which of the transducer elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processing unit (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates RF data and generates raw data. In another embodiment, the demodulation can be carried out earlier in the processing chain.

The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay (e.g., substantially at the time of occurrence). For example, an embodiment may acquire images or 3D volumes at a real-time rate of 7-20 frames/sec. The ultrasound imaging system 100 may acquire two-dimensional (2D) data of one or more planes at a significantly faster rate. However, it should be understood that the real-time frame-rate may be dependent on a length (e.g., duration) of time that it takes to acquire and/or process each frame of data for display. Accordingly, when acquiring a relatively large amount of data, the real-time frame-rate may be slower. For example, the ultrasound imaging system 100 may additionally or alternatively acquire three-dimensional (3D) data. Thus, some embodiments may have real-time frame-rates that are considerably faster than 20 frames/sec while other embodiments may have real-time frame-rates slower than 7 frames/sec.

In some embodiments, the data may be stored temporarily in a buffer (not shown) during a scanning session and processed in less than real-time in a live or off-line (e.g., freeze) operation. Some embodiments of the disclosure may include multiple processors (not shown) to handle the processing tasks that are handled by the processor 116 according to the exemplary embodiment described hereinabove. For example, a first processor may be utilized to demodulate and decimate the RF signal while a second processor may be used to further process the data, for example, by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on the display device 118. Other embodiments may acquire and display data at different rates. For example, some embodiments may acquire data at a frame-rate of less than 10 Hz or greater than 30 Hz depending on the size of the frame and the intended application. The memory 120 may store processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 to form 2D or 3D images. When multiple images are obtained, the processor 116 may also be configured to stabilize or register the images. For example, one or more modules may generate B-mode, color Doppler, M-mode, color M-mode, color flow imaging, spectral Doppler, elastography, tissue velocity imaging (TVI), strain, strain rate, and the like, and combinations thereof. As one example, the one or more modules may process color Doppler data, which may include traditional color flow Doppler, power Doppler, high-definition (HD) flow Doppler, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real-time while a procedure (e.g., ultrasound imaging) is being performed on a patient. The video processor module may include a separate image memory, and the ultrasound images may be written to the image memory in order to be read and displayed by the display device 118.

Further, the components of the ultrasound imaging system 100 may be coupled to one another to form a single structure, may be separate but located within a common room, or may be remotely located with respect to one another. For example, one or more of the modules described herein may operate in a data server that has a distinct and remote location with respect to other components of the ultrasound imaging system 100, such as the probe 106 and the user interface 115. Optionally, the ultrasound imaging system 100 may be a unitary system that is capable of being moved (e.g., portably) from room to room. For example, the ultrasound imaging system 100 may include wheels or may be transported on a cart, or may comprise a handheld device.

For example, in various embodiments of the present disclosure, one or more components of the ultrasound imaging system 100 may be included in a portable, handheld ultrasound imaging device. For example, the display device 118 and the user interface 115 may be integrated into an exterior surface of the handheld ultrasound imaging device, which may further contain the processor 116 and the memory 120 therein. The probe 106 may comprise a handheld probe in electronic communication with the handheld ultrasound imaging device to collect raw ultrasound data. The transmit beamformer 101, the transmitter 102, the receiver 108, and the receive beamformer 110 may be included in the same or different portions of the ultrasound imaging system 100. For example, the transmit beamformer 101, the transmitter 102, the receiver 108, and the receive beamformer 110 may be included in the handheld ultrasound imaging device, the probe, and combinations thereof.

Referring to FIG. 2, an example medical image processing system 200 is shown. In some embodiments, the medical image processing system 200 is incorporated into a medical imaging system, such as an ultrasound imaging system (e.g., the ultrasound imaging system 100 of FIG. 1), an MRI system, a CT system, a single-photon emission computed tomography (SPECT) system, etc. In some embodiments, at least a portion of the medical image processing system 200 is disposed at a device (e.g., an edge device or server) communicably coupled to the medical imaging system via wired and/or wireless connections. In some embodiments, the medical image processing system 200 is disposed at a separate device (e.g., a workstation) that can receive images from the medical imaging system or from a storage device that stores the images generated by the medical imaging system. The medical image processing system 200 may comprise an image processor 231, a user input device 232, and a display device 233. For example, the image processor 231 may be operatively/communicatively coupled to the user input device 232 and the display device 233.

The image processor 231 includes a processor 204 configured to execute machine-readable instructions stored in non-transitory memory 206. The processor 204 may be single core or multi-core, and the programs executed by the processor 204 may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration. In some embodiments, the processor 204 may include other electronic components capable of carrying out processing functions, such as a digital signal processor, a field-programmable gate array (FPGA), or a graphics board. In some embodiments, the processor 204 may include multiple electronic components capable of carrying out processing functions. For example, the processor 204 may include two or more electronic components selected from a plurality of possible electronic components, including a central processor, a digital signal processor, a field-programmable gate array, and a graphics board. In still further embodiments, the processor 204 may be configured as a graphical processing unit (GPU), including parallel computing architecture and parallel processing capabilities.

In the embodiment shown in FIG. 2, the non-transitory memory 206 stores a 3D generation module 212, medical image data 214, and a visual display module 216. The 3D generation module 212 includes one or more algorithms to process input medical images from the medical image data 214. Specifically, the 3D generation module 212 may generate a 3D pleural surface from 2D and/or 3D ultrasound images, as described with respect to FIG. 3. For example, the 3D generation module 212 may include one or more image recognition algorithms, shape or edge detection algorithms, gradient algorithms, and the like to process input medical images. Additionally or alternatively, the 3D generation module 212 may store instructions for implementing a neural network, such as a convolutional neural network, for detecting pleural surfaces/pleura captured in the medical image data 214 in real-time. For example, the 3D generation module 212 may include trained and/or untrained neural networks and may further include training routines, or parameters (e.g., weights and biases), associated with one or more neural network models stored therein. In some embodiments, the 3D generation module 212 may evaluate the medical image data 214 as it is acquired in real-time. Additionally or alternatively, the 3D generation module 212 may evaluate the medical image data 214 offline, not in real-time.

As an example, when the medical image data 214 includes lung ultrasound data, the identified anatomical feature may include lung pleura, which may be identified by the 3D generation module 212 based on pleural sliding via edge detection techniques and/or gradient changes. As will be elaborated with respect to FIG. 3, detection of pleural positioning may assist in indicating a region of an ultrasound image which is noise and may be removed to expose a pleural surface.

Optionally, the image processor 231 may be communicatively coupled to a training module 210, which includes instructions for training one or more of the machine learning models stored in the 3D generation module 212. The training module 210 may include instructions that, when executed by a processor, cause the processor to build a model (e.g., a mathematical model) based on sample data to make predictions or decisions regarding the detection and classification of anatomical irregularities without the explicit programming of a conventional algorithm that does not utilize machine learning. In one example, the training module 210 includes instructions for receiving training data sets from the medical image data 214. The training data sets comprise sets of medical images, associated ground truth labels/images, and associated model outputs for use in training one or more of the machine learning models stored in the 3D generation module 212. The training module 210 may receive medical images, associated ground truth labels/images, and associated model outputs for use in training the one or more machine learning models from sources other than the medical image data 214, such as other image processing systems, the cloud, etc. In some embodiments, one or more aspects of the training module 210 may include remotely-accessible networked storage devices configured in a cloud computing configuration. Further, in some embodiments, the training module 210 is included in the non-transitory memory 206. Additionally or alternatively, in some embodiments, the training module 210 may be used to generate the 3D generation module 212 offline and remote from the medical image processing system 200. In such embodiments, the training module 210 may not be included in the medical image processing system 200 but may generate data stored in the medical image processing system 200. For example, the 3D generation module 212 may be pre-trained with the training module 210 at a place of manufacture.

The non-transitory memory 206 further stores the medical image data 214. The medical image data 214 includes, for example, functional and/or anatomical images captured by an imaging modality, such as an ultrasound imaging system, an MRI system, a CT system, a PET system, etc. As one example, the medical image data 214 may include ultrasound images, such as lung ultrasound images. Further, the medical image data 214 may include one or more of 2D images, 3D volumes, 3D images, static single frame images, and multi-frame cine-loops (e.g., movies).

The visual display module 216 includes one or more algorithms to process 3D pleural surfaces generated by the 3D generation module 212 to facilitate visualization of the 3D pleural surfaces in a manner that may aid in clinical interpretation of the 3D pleural surfaces. As will be elaborated with respect to FIG. 5, the visual display module 216 may be configured to shade the 3D pleural surfaces and apply color to the 3D pleural surfaces based on depth in order to facilitate topographic visualization of the 3D pleural surfaces. Additionally, certain features present below the pleural surface may be visualized via the visual display module 216 as volume renderings, such as B lines and consolidations.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices in a cloud computing configuration. As one example, the non-transitory memory 206 may be part of a picture archiving and communication system (PACS) that is configured to store patient medical histories, imaging data, test results, diagnosis information, management information, and/or scheduling information, for example.

The medical image processing system 200 may further include the user input device 232. The user input device 232 may comprise one or more of a touchscreen, a keyboard, a mouse, a trackpad, a motion sensing camera, or other device configured to enable a user to interact with and manipulate data stored within the image processor 231.

The display device 233 may include one or more display devices utilizing any type of display technology. In some embodiments, the display device 233 may comprise a computer monitor and may display unprocessed images, processed images, parametric maps, and/or exam reports. The display device 233 may be combined with the processor 204, the non-transitory memory 206, and/or the user input device 232 in a shared enclosure or may be a peripheral display device. The display device 233 may include a monitor, a touchscreen, a projector, or another type of display device, which may enable a user to view medical images and/or interact with various data stored in the non-transitory memory 206. In some embodiments, the display device 233 may be included in a smartphone, a tablet, a smartwatch, or the like.

It may be understood that the medical image processing system 200 shown in FIG. 2 is one non-limiting embodiment of an image processing system, and other imaging processing systems may include more, fewer, or different components without departing from the scope of this disclosure. Further, in some embodiments, at least portions of the medical image processing system 200 may be included in the ultrasound imaging system 100 of FIG. 1, or vice versa (e.g., at least portions of the ultrasound imaging system 100 may be included in the medical image processing system 200).

As used herein, the terms "system" and "module" may include a hardware and/or software system that operates to perform one or more functions. For example, a module or system may include or may be included in a computer processor, controller, or other logic-based device that performs operations based on instructions stored on a tangible and non-transitory computer readable storage medium, such as a computer memory. Alternatively, a module or system may include a hard-wired device that performs operations based on hard-wired logic of the device. Various modules or systems shown in the attached figures may represent the hardware that operates based on software or hardwired instructions, the software that directs hardware to perform the operations, or a combination thereof.

"Systems" or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Figure 3:
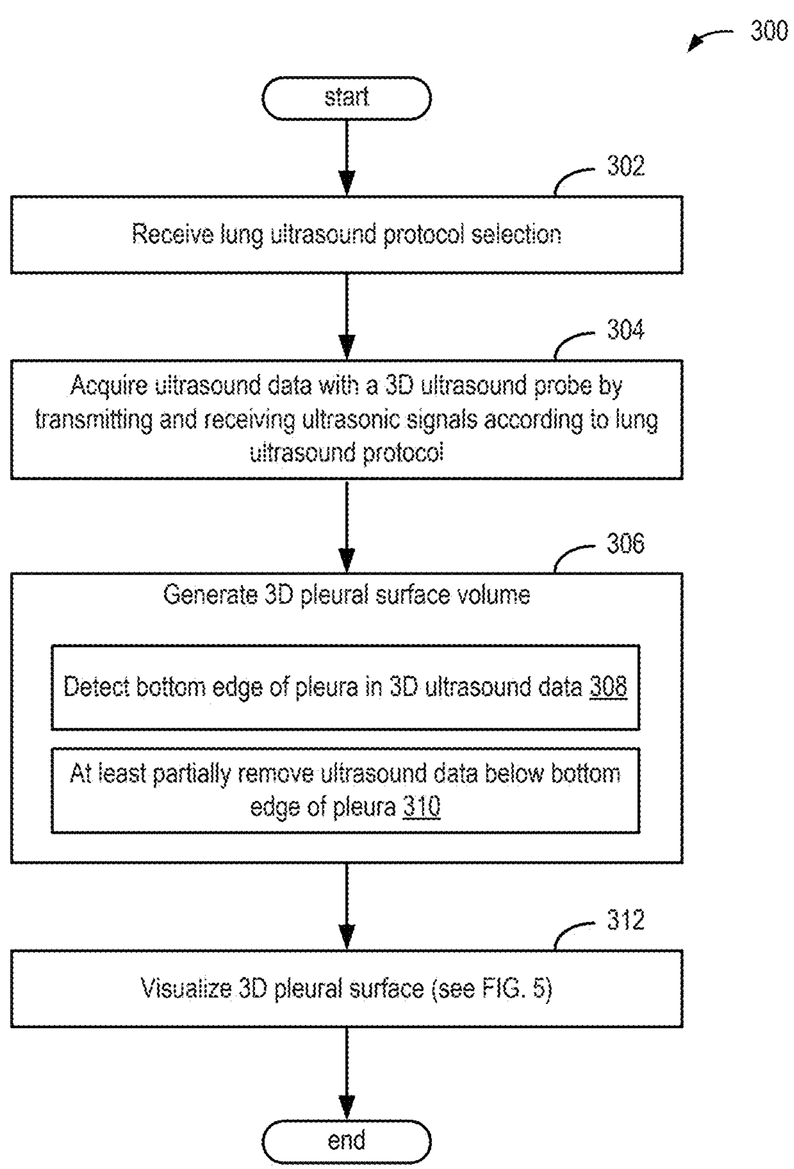
FIG. 3 shows a flowchart illustrating an example method for generating 3D pleural surface volumes, according to an embodiment.

FIG. 3 shows a flow chart for an example method 300 for generating a 3D pleural surface, where ultrasound imaging signals used to generate the 3D pleural surface are acquired using a probe capable of live 3D imaging, such as a matrix array probe or other volumetric probe, to acquire a 3D volume. In particular, the method 300 provides a workflow for generating the 3D pleural surface from a 3D volume captured using the probe capable of live 3D imaging by identifying a pleural line in the 3D volume and adjusting aspects (e.g., transparency) of the 3D volume at and/or below the pleural line to expose the 3D pleural surface. Method 300 will be described for 3D ultrasound volumes acquired using an ultrasound imaging system, such as ultrasound imaging system 100 of FIG. 1, although other ultrasound imaging systems may be used. Further, method 300 may be adapted to other imaging modalities. Method 300 may be implemented by one or more of the above described systems, including the ultrasound imaging system 100 of FIG. 1 and medical image processing system 200 of FIG. 2. As such, method 300 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2. Further, in some embodiments, method 300 is performed in real-time, as the 3D volumes are acquired, while in other embodiments, at least portions of method 300 are performed offline, after the 3D volume is acquired. For example, the processor may evaluate 3D volumes that are stored in memory even while the ultrasound system is not actively being operated to acquire images.

At 302, method 300 includes receiving a lung ultrasound protocol selection. The lung ultrasound protocol may be selected by an operator (e.g., user) of the ultrasound imaging system via a user interface (e.g., the user interface 115). As one example, the operator may select the lung ultrasound protocol from a plurality of possible ultrasound protocols using a drop-down menu or by selecting a virtual button. Alternatively, the system may automatically select the protocol based on data received from an electronic health record (EHR) associated with the patient. For example, the EHR may include previously performed exams, diagnoses, and current treatments, which may be used to select the lung ultrasound protocol. Further, in some examples, the operator may manually input and/or update parameters to use for the lung ultrasound protocol. The lung ultrasound protocol may be a system guided protocol, where the system guides the operator through the protocol step-by-step, or a user guided protocol, where the operator follows a lab-defined or self-defined protocol without the system enforcing a specific protocol or having prior knowledge of the protocol steps.

Further, the lung ultrasound protocol may include a plurality of scanning sites (e.g., views), probe movements, and/or imaging modes that are sequentially performed. For example, the lung ultrasound protocol may include using dynamic M-mode. The lung ultrasound protocol may include a longitudinal scan, wherein the probe is positioned perpendicular to the ribs, and/or an oblique scan, wherein the probe is positioned along intercostal spaces between ribs. Further still, in examples where the ultrasound probe is a matrix probe, the lung ultrasound protocol may include indicating a static position on the patient at which to hold the ultrasound probe while volumetric ultrasound data is captured by the ultrasound probe.

At 304, method 300 includes acquiring ultrasound data with the ultrasound probe by transmitting and receiving ultrasonic signals according to the lung ultrasound protocol. Acquiring ultrasound data according to the lung ultrasound protocol may include the system displaying instructions on the user interface, for example, to guide the operator through the acquisition of the designated scanning sites. Additionally or alternatively, the lung ultrasound protocol may include instructions for the ultrasound system to automatically acquire some or all of the data or perform other functions. For example, the lung ultrasound protocol may include instructions for the user to position, move, rotate, tilt, and/or sweep the ultrasound probe, as well as to automatically initiate and/or terminate a scanning process and/or adjust imaging parameters of the ultrasound probe, such as ultrasound signal transmission parameters, ultrasound signal receive parameters, ultrasound signal processing parameters, or ultrasound signal display parameters. In some embodiments, live 3D image data may be acquired by a matrix 2D probe, or by a mechanically-wobbling 1D probe.

At 306, method 300 includes generating a 3D pleural surface volume from the acquired ultrasound data. For example, the signal data acquired from the ultrasound imaging system 100 is processed and analyzed by the processor in order to produce a 3D pleural surface volume at a designated frame rate. The processor may include an image processing module that receives the signal data (e.g., image data) acquired from the ultrasound imaging system 100 and processes the received image data. The 3D pleural surface volume may allow visualization of a pleural surface as if viewed from an inside of the lung and looking outward based on a volume of ultrasound data (e.g., the acquired ultrasound data).

Generating the 3D pleural surface volume may include, at 308, detecting a bottom edge of the pleura in the 3D ultrasound data. In an aerated lung, the pleura, which form the outer boundary of the lung that lies against the chest wall, may provide the substantially only anatomical lung structure detectable by ultrasound. The pleura appear as a hyperechoic horizontal segment of brighter (e.g., whiter) pixels in an ultrasound image, referred to as a pleural line, which moves synchronously with respiration in a phenomenon known as pleural sliding. Detecting the bottom edge of the pleura may include detecting the interface between tissue and air, which may include identifying lower and upper borders of the pleura (e.g., identifying the pleural line) based on a brightness change between pixels, such as by using edge detection techniques or gradient changes. For example, the 3D volume acquired at 304 may be comprised of a plurality of 2D slices (e.g., 100-200 slices/frames). For each 2D slice, the processor may apply an edge detection algorithm, such as included in the 3D generation module 212 of FIG. 2, that comprises one or more mathematical methods for identifying points (e.g., pixels) at which the image brightness changes sharply and/or has discontinuities to identify the lower and upper borders of the pleural line. As one example, the processor may apply the edge detection algorithm to the area having the highest amount of local change. As another example, additionally or alternatively, a gradient algorithm may identify a local maximum and/or minimum pixel brightness at the pleura to identify the lower and upper borders of the pleural line in each 2D slice, across a plurality of frames of ultrasound data. For example, the ultrasound data acquired at 304 may be 4D ultrasound data where a plurality of 3D volumes are acquired over time, with each 3D volume referred to as a frame of ultrasound data. Each 3D volume may comprise a plurality of 2D slices that are evaluated as explained above. In frames without pleural sliding (e.g., between breaths), the location of the pleura may be tracked up/down based on its known location from the previous frame. Once the pleura line in all slices/frames of the volume are identified, the pleural surface is generated as a 3D mesh that links together all pleural lines from all frames. Other mechanisms for detecting the pleural line in the 3D volume are possible. For example, the 3D ultrasound data may be volume rendered into a 3D image at a selected viewpoint using ray casting or another suitable technique. The mechanisms for detecting the pleural line described above (e.g., identifying lower and upper borders of the pleura based on a brightness change between pixels, such as by using edge detection techniques or gradient changes) may then be applied to the 3D image.

The lower and upper borders of the pleura may include sub pleural consolidations. For example, the bottom edge (e.g., indicating a boundary below which to remove or suppress ultrasound data, as further described herein) may be positioned a predetermined distance towards the lung from the pleural line. It may be understood that, conventionally, sub pleural consolidations extend a maximum distance 'n' from the pleural surface towards the lung. Thus, the bottom edge of the pleura may be positioned a distance 'n' from the lower border of the pleura identified as described above. In other embodiments, sub pleural consolidations may be identified using the same or a different edge detection algorithm described above.

Following identification of the pleural line, method 300 includes, at 310, at least partially removing ultrasound data from below the bottom edge of the pleural line. At least some of the ultrasound data below the bottom edge of the pleural line may be suppressed or removed from the 3D ultrasound data (e.g., the volume) to form a new volume (e.g., the 3D pleural surface volume) or at least some of the ultrasound data below the bottom edge of the pleural line may be removed from the 3D image to form a 3D pleural surface image. Ultrasound imaging data vertically below the bottom edge of the pleural line may be noise that does not indicate the topography of the pleural line. Removing ultrasound data from below the bottom edge of the pleural line may expose the topography of the pleural line. Removing ultrasound data may include generating a new dataset for each ultrasound volume, the new dataset including ultrasound data above and including the pleural line, and excluding data below the bottom edge of the pleural line (e.g., noise). In other examples, at least partially removing the ultrasound data from below the bottom edge of the pleural line includes adjusting the transparency of at least some of the voxels below the pleural line. For example, the voxels below the bottom edge of the pleural line may be set to 100% transparency. In still further examples, as will be explained in more detail below, at least some anatomical features (e.g., B-lines) below the bottom edge of the pleural line may be maintained in the 3D image or volume and thus only voxels having a brightness below a threshold may be removed (or set to 100% transparency). In still further examples, the voxels below the bottom edge of the pleural line may be partially removed/suppressed by increasing the transparency of the voxels below the bottom edge of the pleural line. For example, the voxels that constitute the pleural line may be set to 0% transparency and the voxels below the bottom edge of the pleural line may be set to a transparency that is greater than 0% but less than 100% (e.g., 50%, 75%).

Figure 4:
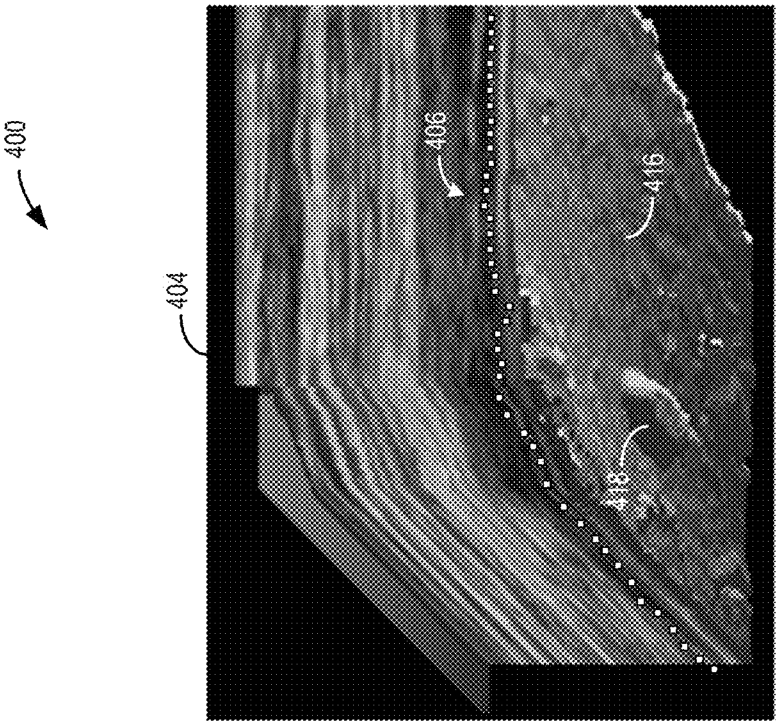
FIG. 4 shows an example set of images generated according to the method of FIG. 3.
Figure 4:
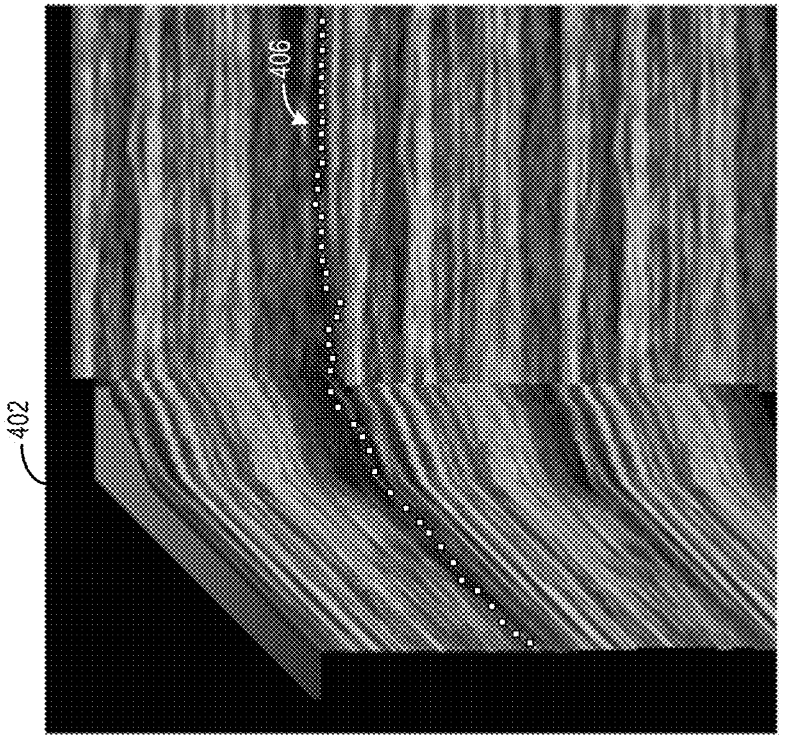

Turning briefly to FIG. 4, an example set of images 400 is shown, including a 3D ultrasound image 402 and a 3D pleural surface image 404. The 3D ultrasound image 402 may be a surface rendering of the 3D volume of ultrasound data acquired using a volumetric probe (e.g., at operation 304 of method 300) that shows outer sides of the volume. The 3D pleural surface image 404 may be generated from the 3D volume of ultrasound data by setting the transparency of the voxels along the pleural surface to 0% (100% opacity) and setting the transparency of the voxels below the pleural surface to 100% (0% opacity) and then volume rendering the 3D volume from the inside-out, as described with respect to the method 300. The 3D pleural surface image 404 may essentially be a perspective view of a cross-section of the 3D volume taken across the volume at the bottom edge of the pleura. Each of the 3D ultrasound image 402 and the 3D pleural surface image 404 may include pleural line indicators 406, which may be generated at operation 306 of the method 300. The pleural line indicators 406 may be positioned on a lower boundary (e.g., the bottom edge) of the pleural line and may visually indicate pixels of the 3D ultrasound image 402 which are identified as the pleural line. In other examples, the pleural line may be traced (e.g., with a continuous line) to visually indicate the pleural line in the 3D ultrasound image 402. Removing/suppressing ultrasound data from below the pleural line may include removing/suppressing ultrasound data below the pleural line indicators 406. As a vertical location of each of the pleural line indicators 406 may be different and may reflect a curvature, protrusion, and/or other irregularities in the pleural line, removal of ultrasound data below the pleural line indicators 406 results in a topographical pleural surface 416 which includes protrusions into the inside of the lung, such as a protrusion 418.

Returning to FIG. 3, at 312, the method 300 includes visualizing the 3D pleural surface, which is explained in more detail below with respect to FIG. 5. Briefly, one or more images of the 3D pleural surface volume that visualize the pleural surface may be rendered for display on a display device. In some examples, the display is included in the ultrasound imaging system, such as display device 118. The one or more images may be rendered with surface shading and/or colorized based on relative depth of the plural surface to enhance visualization of the topographic features of the pleural surface. Additionally, the one or more images may include volumetric rendering of features of interest below the pleural surface, such as B lines.

Figure 5:
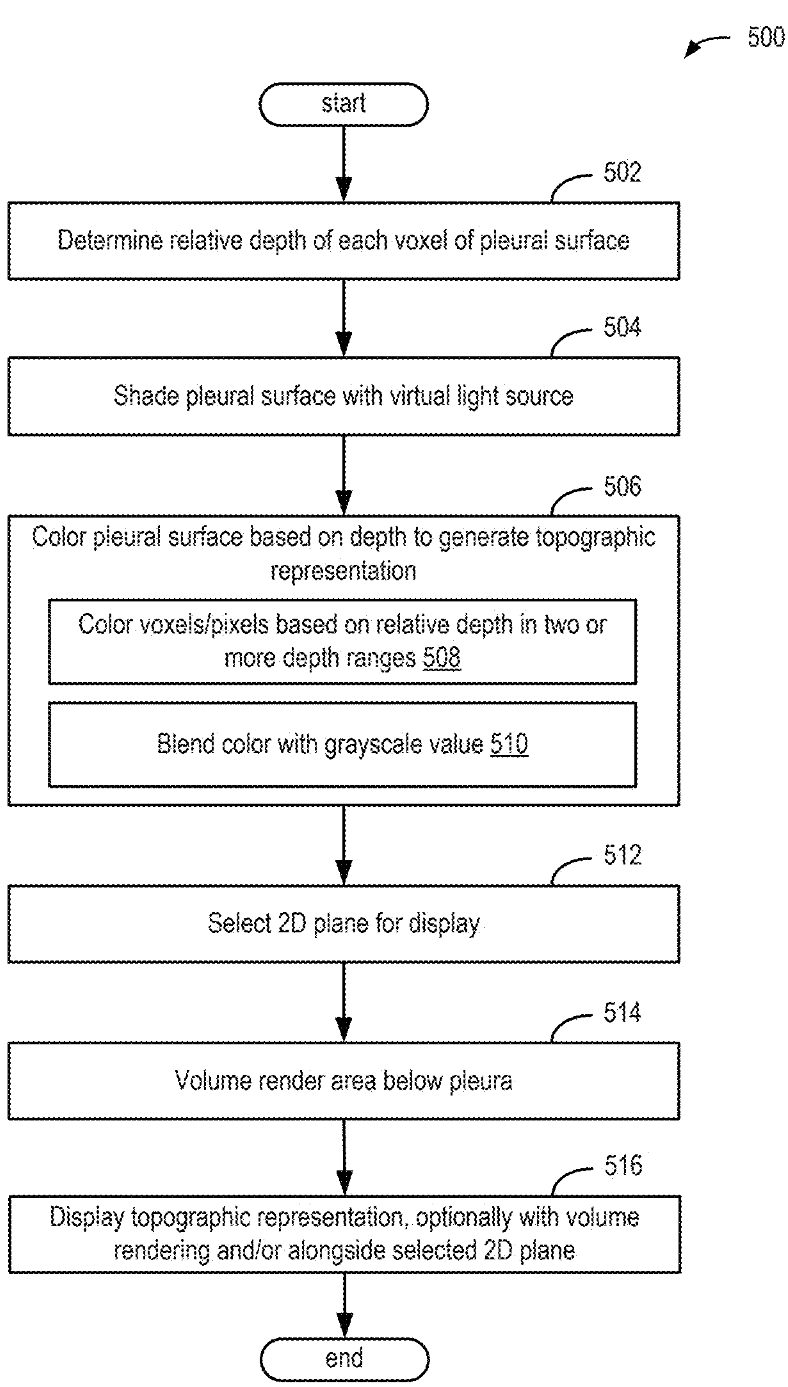
FIG. 5 shows a flowchart illustrating an example method for visualizing a 3D pleural surface of a 3D pleural surface volume, according to an embodiment.
Figure 6:
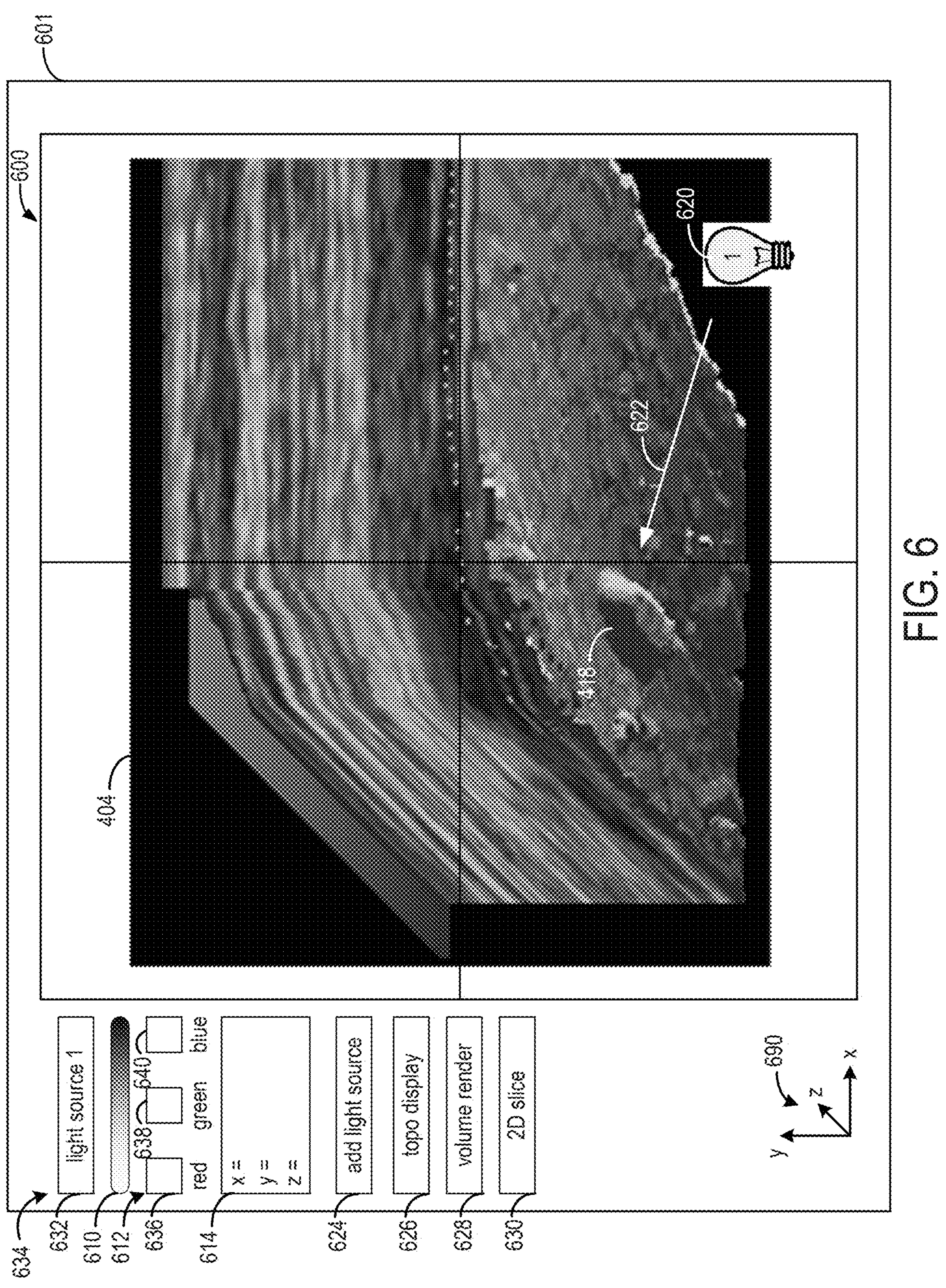
FIGS. 6-10 show example interfaces displaying a 3D pleural surface.

FIG. 5 shows a flowchart illustrating an example method 500 for visualizing a 3D pleural surface of a 3D pleural surface image or a 3D pleural surface volume, for example, the 3D pleural surface image or the 3D pleural surface generated as described with respect to FIG. 3. In particular, method 500 provides a workflow for forming and shading a topographic representation of a pleural surface and for coloring the topographic representation based on the relative depth of pixels or voxels within the topographic representation. Method 500 may be implemented by one or more of the above described systems, including the ultrasound imaging system 100 of FIG. 1 and medical image processing system 200 of FIG. 2. As such, method 500 may be stored as executable instructions in non-transitory memory, such as the memory 120 of FIG. 1 and/or the non-transitory memory 206 of FIG. 2, and executed by a processor, such as the processor 116 of FIG. 1 and/or the processor 204 of FIG. 2. In some examples, method 500 may be performed as part of method 300, such as at 312 of method 300.

At 502, the method 500 includes determining the relative depth of each voxel of the pleural surface in the 3D pleural surface volume. The relative depth may be determined as the depth of a voxel included in the pleural surface from a baseline (e.g., expected pleural line). The baseline may be a surface approximation. In some examples, the surface approximation may be a line of best fit applied to one or more sections of the pleural surface. The line of best fit may be a linear approximation of the pleural surface. For example, a line of best fit may be applied for the pixels or voxels identified as the pleural line, e.g., for each slice of the volume, such that the surface approximation is comprised of a plurality of lines of best fit, one for each slice of the volume. The relative depth of a voxel may be calculated by determining the distance and direction of each voxel from the surface approximation/line of best fit (e.g., the expected pleural line). It is to be appreciated that the pleura is not always horizontal. In some rib locations, and in some scanning circumstances, the pleura may appear as a diagonal line. Thus, the relative depth of each voxel may be determined as an orthogonal deviation from the expected pleural line.

At 504, the method 500 includes shading the pleural surface with a virtual light source as if inside the lung. As described with respect to FIG. 3, the 3D pleural surface is viewed from the inside of the lung and looking outward (e.g., a region below the pleural surface in the 3D pleural surface is considered inside the lung). The virtual light source may be positioned such that, when illuminated, the virtual light source directs light towards the pleural surface. The virtual light source may be positioned in a pre-set location with respect to the pleural surface, such as a bottom right, top left, bottom left, or top right of a display. In some examples, the virtual light source may be positioned with respect to an identified protrusion. In some examples, a protrusion may be identified by evaluating each voxel of the pleural line to determine a jumpiness score and a dimness score for each pleural location in order to identify positions of pleural irregularities. The jumpiness score evaluates a vertical location of the pleural line at each horizontal location to identify vertical gaps in the pleural line, with a greater vertical gap resulting in a higher jumpiness score. For example, the vertical gap may refer to a number of pixels vertically between the lower border (or upper border) of the pleural line at the given pixel location relative to a neighboring pixel. The vertical gap between the upper or lower border of the pleural line at neighboring horizontal locations may result in the pleural line having a discontinuous or rough appearance, for example. In some examples, the relative depth of each voxel may be used to identify pleural irregularities, wherein the distance from each voxel to the surface approximation may be used to calculate the jumpiness score. The dimness score ranks the pleural voxel brightness (or dimness) at a particular horizontal location relative to its neighbors. As the local voxel brightness of the pleura decreases relative to its neighbors (e.g., the pixel becomes more dim relative to its neighbors), the dimness score increases.

An irregularity score for each voxel along the pleural line in each frame may be generated as a product of the jumpiness score and the dimness score and compared to a threshold score. The threshold score may be a pre-determined value stored in memory that distinguishes irregular pleura associated with a disease state from normal, healthy pleura.

In some examples, the threshold score may be adjusted based on curated data and using a support vector machine. If the irregularity score is greater than or equal to the threshold score, the pleura imaged in that voxel location may be considered irregular. In contrast, if the irregularity score is less than the threshold score, the pleura imaged in that pixel location may not be considered irregular (e.g., may be considered normal and/or healthy). Although the pleura may be analyzed on a voxel-by-voxel basis, a filter may be used to smooth the results. As a result, an area of voxels having pre-determined dimensions may be grouped and identified as a location of irregularity (e.g., irregular pleura) responsive to a majority (e.g., greater than 50%) of the voxels within the group being characterized as irregular pleura (e.g., a protrusion). In contrast, the area of voxels may be identified as healthy responsive to the majority of the voxels within the group being characterized as healthy pleura.

For example, when the identified protrusion is in a top left quadrant of a display, the virtual light source may be positioned in a bottom right quadrant of the display. The brightness of the virtual light source may be adjusted. The virtual light source may emit light radially, linearly, or as a ray, for example, and a shape of emitted light may be adjusted in response to user input. A brightness and a color/tint of the virtual light source may further be adjusted in response to user input.

In some examples, the virtual light source may be automatically positioned at pre-set or random coordinates within the inside of the lung which corresponds with the 3D pleural surface. Coordinates of the virtual light source may be shown in a coordinate selector. The virtual light source may be positioned with respect to an identified protrusion in the 3D pleural surface (e.g., which extends towards the inside of the lung). For example, one or more protrusions of the 3D pleural surface may be identified, and the virtual light source may be positioned at coordinates where the virtual light source, and light beam cast by the virtual light source, is at an acute angle with respect to the 3D pleural surface. In this way, the virtual light source may highlight the protrusion extending from the pleural surface towards the inside of the left lung. This may assist a user, such as a healthcare provider or imaging technician viewing the display to quickly and accurately identify pleural irregularities in the 3D pleural surface, which may help reduce a diagnosis timeline and increase an accuracy of diagnosis.

At 506, the method may include coloring the pleural surface based on depth (e.g., orthogonal deviation) to generate a topographic representation of the pleural surface. Coloring the pleural surface based on depth/orthogonal deviation may include, at 508, coloring the voxels in the pleural surface based on relative depth/orthogonal deviation in two or more depth/deviation ranges. Each depth/deviation range may encompass a range of relative depths/orthogonal deviations (e.g., relative to the baseline/expected pleural line, as explained above), and each depth/deviation range may be associated with a color. For example, a first depth range may include relative depths/orthogonal deviations that do not deviate significantly from the expected pleural line, such as deviations between −1 and 1 mm relative to the expected pleural surface. Negative deviation values may be used to indicate depths/orthogonal deviations corresponding to depressions in the pleural surface (e.g., viewed from the inside of the lung looking outward, and thus a depression may extend from the pleural surface towards the outside of the lung), while positive deviation values may be used to indicate depths/orthogonal deviations corresponding to protrusions in the pleural surface (e.g., viewed from the inside of the lung looking outward, and thus a protrusion may extend from the pleural surface towards the inside of the lung). The first depth range may not be associated with a color, and thus voxels included in the first depth range may be rendered in grayscale. A second depth range may include relative depths/orthogonal deviations greater than the first depth range (e.g., greater than 1 mm), and may have a first color associated with it, such as red. A third depth range may include relative depths/orthogonal deviations less than the first depth range (e.g., less than −1 mm) and may have a second color associated with it, such as blue. In some examples, more depth ranges may be included to display the degree to which the relative depth of a voxel differs from a normal range. For example, voxels that are at a depth greater than baseline may be sorted into two or more depth ranges. In one example, as explained above, the first depth range may represent baseline topology and may include voxel/pixel depths between −1 and 1 mm. Depths greater than 1 mm may be divided into two or more depth ranges. A third depth range may represent mild to moderate deviation from baseline topology, such as depths between 1 and 3 mm and may be colored yellow. A fourth depth range may represent larger deviation from baseline topology, such as depths greater than 3 mm and may be colored red, for example. Further, in some examples, different depth ranges may be applied for different patient populations. For example, in adult populations, depths greater than 3 mm relative to baseline may be considered a large deviation and thus colored red, while in pediatric patients, depths greater than 1 or 2 mm relative to baseline may be considered a large deviation and thus colored red. The differential depth ranges may be applied automatically based on a scan protocol being executed, patient information, etc., or the differential depth ranges may be applied based on user input, as explained in more detail below.

In some examples, coloring the plural surface may include, at 510, blending the color assigned to each voxel with the underlying grayscale value. Each voxel includes a grayscale value based on the received ultrasound data, which may be used by clinicians to appreciate the echogenicity of the imaged anatomical features. To retain the information contained in the grayscale value of each voxel, color may be overlaid transparently over the grayscale of each voxel. A color overlaid upon multiple voxels with different grayscale values may appear differently when rendered for display. For example, a voxel that is white in grayscale may be highly saturated in color, while the color saturation of a voxel that is dark gray in grayscale may be less saturated. The intensity of the color (e.g., opacity/transparency) overlaid over the grayscale values may be adjusted automatically or by user input to ensure that the grayscale value of each voxel is visible and the color associated with each voxel is visible when rendered.

At 512, the method 500 may optionally include selecting a 2D plane from the 3D ultrasound data for display. The 2D plane may be a cross sectional view of the entire 3D volume of ultrasound data, including the pleural surface, and may be useful to show protrusions or depressions in the pleural surface in profile. In some examples, a 2D plane may be selected automatically based on the depth of the protrusion or depression present in the 2D plane. In some examples, a 2D plane that shows a cross section of the deepest protrusion or depression may be automatically selected for display. In other examples, the 2D plane may be selected by a user.

At 514, the method 500 may include optionally volume rendering the area below the pleura. In some examples, the area below the pleura may include features that may be useful for a clinician to view, such as B-lines and pleural consolidations. In some examples, the entire area below the pleura (e.g., the data below the bottom edge of the pleura that was removed to create the 3D pleural surface volume) may be volume rendered to form a volume rendering (which may be a 2D projection of the volume below the pleura) at the same view angle as the 3D pleural surface volume/topographic representation, to be displayed along with the topographic representation. In some examples, volume rendering may be accomplished using a suitable method, such as ray casting/tracing, maximum intensity projection, or minimum intensity projection. Maximum intensity projection may project each voxel with the maximum intensity that falls in the path of respective parallel rays between the viewpoint and the image being rendered. Maximum intensity projection may make voxels with the greatest intensity more easily visible, which may allow features such as B-lines to be more easily visible. Ray casting/tracing may include casting a ray for each pixel of the final volume rendering through the volume, shading a plurality of sample points along each ray (wherein each sample point is where the ray intersects a voxel or an interpolation between multiple voxels, if the sample point does not intersect a voxel), and compositing the shaded sample points. The rays used to perform the projection may be based on the view angle of the 3D pleural surface volume/topographic representation. In some examples, the area below the pleural surface may be rendered separately from the 3D pleural surface volume and overlaid on an image rendered from the 3D pleural surface volume. In other examples, the entire 3D volume of ultrasound data may be volume rendered as explained above (e.g., using ray casting/tracing with the view angle being inside-out), with the pleural surface shaded and colored as explained above (e.g., the pleural surface set to 0% transparency and colored based on depth) and the voxels below the pleural surface having increased transparency, such that the remainder of the ultrasound data below the pleural line being the volume rendering of the area below the pleura. Because the voxels below the pleural line have increased transparency, anatomical features below the pleura such as B lines may be visualized while noise or otherwise anatomically-irrelevant features are suppressed and not visualized.

Figure 9:
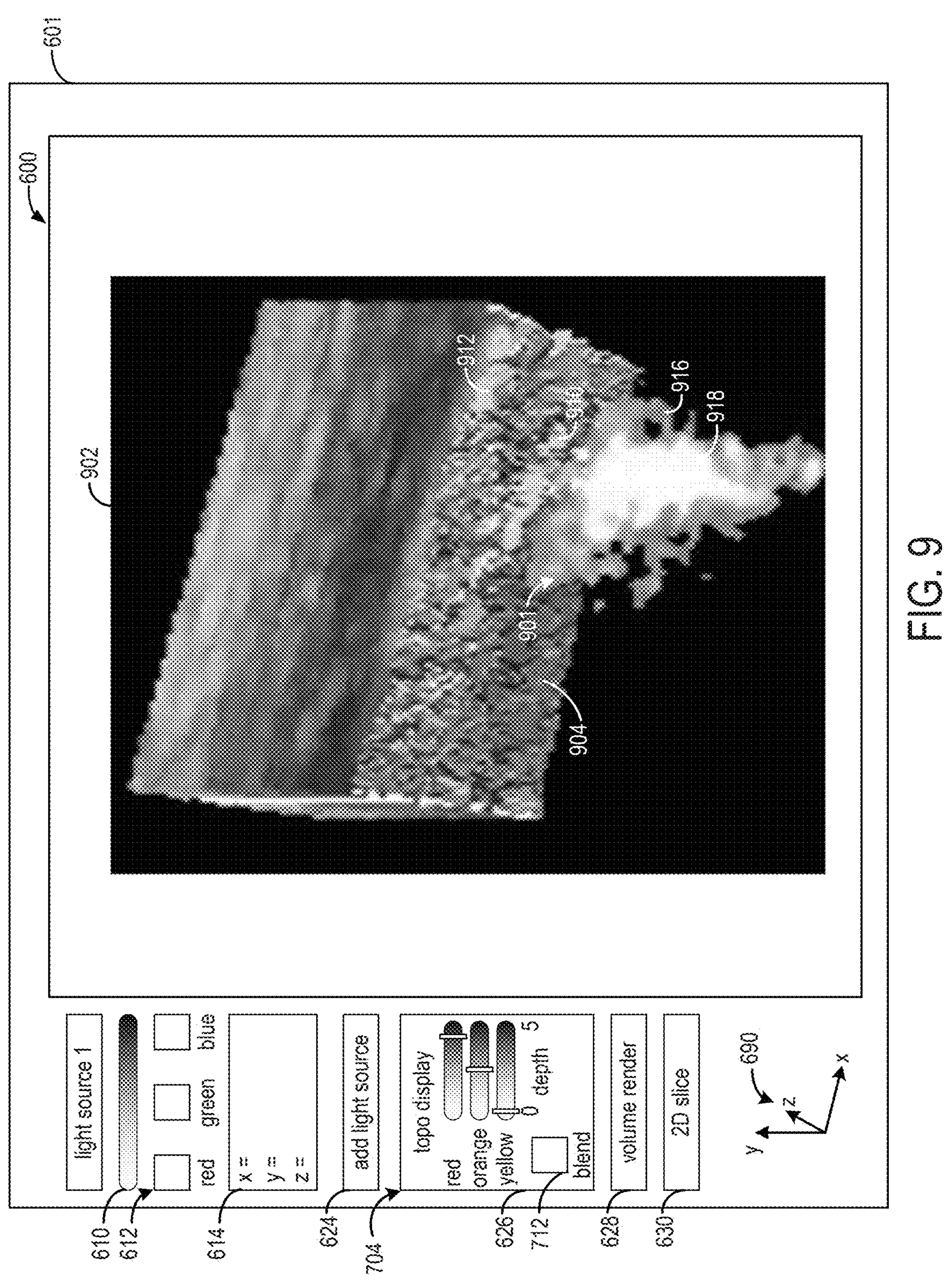

In some examples, features of interest in the volume rendering of the area below the pleura may be colored and/or the volume rendering of the area below the pleura may be filtered such that only the features of interest may be displayed. For example, during ray casting, the shading may be performed such that only voxels above a brightness threshold may be shaded. For example, B-lines may appear as linear areas of high brightness. The volume rendering may also use opacity and transparency parameters so that the volume below the pleura is semi-transparent while the pleura surface itself is rendered as an opaque or solid surface. Semi-transparency of the volume below the pleura may be adjusted so that B lines, which extend below the pleura, are still rendered and visible. An example of an image wherein the area below the pleura has been volume rendered is shown in FIG. 9 and explained in more detail below, wherein a pleural consolidation is visible beneath the pleura.

At 516, the method 516 may include displaying the topographic representation of the 3D pleural surface, optionally with the volume rendering of the area below the pleura and/or alongside the selected 2D plane. The topographic representation may be a perspective view of the 3D pleural surface volume, positioned in such a way that the pleural surface is shown as the bottom surface of the volume, due to volume rendering of the 3D pleural surface volume. The topographic representation may be displayed in the perspective view as a default view, or a particular view may be automatically selected to display the protrusions or depressions that may be most indicative of pathology. The topographic representation may be displayed on a graphical user interface (GUI) and one or more display options for the topographic representation may be selected and/or adjusted by a user via elements of the GUI. In some examples, the angle of the 3D pleural surface volume viewed in the displayed topographic representation (e.g., the view angle/perspective of the topographic representation of the pleural surface) may be adjusted via the GUI, and other viewing options such as panning, zooming, rotating, and spinning may be available to allow a user to view the pleural surface (with the pleural surface colored based on depth) from a desired viewpoint. Display options may include whether or not to display the volume rendering of the area below the pleura and/or selected 2D image, and/or options for coloring the pleural surface of the topographic representation. In some examples, the 3D pleural surface volume may be displayed as a static volume that can be viewed from multiple angles.

In some examples, the pleural surface volume may be captured in 4D, e.g., a 3D volume captured over time. In some examples, approximately 25 volumes may be captured per second by the ultrasound imaging system 100. The 3D volumes may be processed to form 3D pleural surface volumes (as explained above with respect to FIG. 3) that include the voxels of the pleural surface being colorized based on depth (e.g., as explained above), and displayed (e.g., volume rendered) in real time to produce a real time topographic representation of the pleural surface, which may be helpful for viewing lung anatomy during breathing. In some examples, the term "real time" is defined to include a procedure that is performed without any intentional delay (e.g., substantially at the time of occurrence). This may include analyzing and processing the 3D volumes as they are received by the image processor 231, which may present a real time video of the pleural surface with the pleural surface colorized based on the relative depth/orthogonal deviation of the pleural surface compared to the baseline pleural surface. The coloring may be applied as each volume is obtained, and while further volumes are being obtained. In one example, the ultrasound imaging system 100 may acquire approximately 25 volumes per second. However, it should be understood that the real-time frame-rate may be dependent on a length (e.g., duration) of time that it takes to acquire and/or process each frame of data for display. In some examples, each volume acquired by the ultrasound imaging system 100 may be processed and analyzed according to the method 500. Accordingly, when acquiring a relatively large amount of data, the real-time frame-rate may be slower. Thus, some embodiments may have real-time frame-rates that are approximately 25 volumes/second while other embodiments may have real-time frame-rates slower than 7 volumes/second. By detecting the pleura surface in the 3D volume first and then assigning higher transparency values to voxels below the pleura and 0 transparency (full opacity) for the voxels along the pleura surface, the volume rendering can be achieved in a single step of rotation of the entire volume. This saves processing power and time.

FIG. 6 shows an example interface 600 (e.g., an example GUI) displaying the 3D pleural surface image 404 that may be output to a display 601. The display 601 may be the display device 118 of FIG. 1, for example, or the display device 233 of FIG. 2. The interface 600 may include sliders for adjusting a brightness (e.g., a brightness selector 610), a color/tint (e.g., hue boxes 612), and a position (e.g., a coordinate selector 614) of one or more light sources, as well as a Cartesian coordinate system 690. The y-axis may be a vertical axis (e.g., parallel to a gravitational axis), the x-axis may be a lateral axis (e.g., horizontal axis), and the z-axis may be a longitudinal axis, in one example. However, the axes may have other orientations, in other examples.

The 3D pleural surface image 404 is centered on a quadrant grid and oriented such that an outside of a patient is in an upper right and an upper left quadrant, and an inside of a lung of the patient is in a bottom right and a bottom left quadrant of the quadrant grid. The 3D pleural surface image 404 may be constructed by processing raw data into a 3D pleural surface volume according to the method 300 and rendering the 3D pleural surface volume according to the method 500, with the voxels in/along the pleural surface being assigned zero transparency and the voxels below the pleural surface being assigned high/full transparency to form the 3D pleural surface image 404. A virtual light source 620 may be positioned within the interior of the lung and be used to shade the 3D pleural surface image 404. In some examples, the virtual light source 620 may be automatically positioned at pre-set or random coordinates within the inside of the lung which corresponds with the portions of the 3D pleural surface image 404. Coordinates of the virtual light source may be shown in the coordinate selector 614. The virtual light source 620 may be positioned with respect to an identified protrusion in the 3D pleural surface image 404 (e.g., which extends towards the inside of the lung). For example, one or more protrusions of the 3D pleural surface image 404 may be identified, and the virtual light source 620 may be positioned at coordinates where the virtual light source 620, and light beam (e.g., indicated by an arrow 622) cast by the virtual light source 620, is at an acute angle with respect to the pleural surface of the 3D pleural surface image 404. In this way, the virtual light source 620 may highlight the protrusion extending from the topographical pleural surface 416 towards the inside of the lung. This may assist a user, such as a healthcare provider or imaging technician viewing the display 601 to quickly and accurately identify pleural irregularities in the 3D pleural surface, which may help reduce a diagnosis timeline and increase an accuracy of diagnosis.

In some examples, automatically positioning the virtual light source 620 may include identifying a protrusion and positioning the virtual light source 620 in a complementary quadrant. For example, when the protrusion 418 is in the bottom left quadrant, the virtual light source 620 may be automatically positioned in the bottom right quadrant, such that the light beam, indicated by the arrow 622, highlights at least part of the protrusion 418. In examples where a protrusion is in the bottom right quadrant, the virtual light source 620 may be positioned in the bottom left quadrant. In some examples, the virtual light source 620 may be automatically positioned without identifying a protrusion. The virtual light source 620 may be positioned at pre-set or random coordinates in one of the bottom right or the bottom left quadrants. In some examples, the virtual light source 620 may be moved in response to a user input, such as changing coordinates of the virtual light source 620 in the coordinate selector 614, selecting and moving the virtual light source 620 (e.g., dragging a selection tool across the interface 600), selecting on the interface 600 a new position for the virtual light source 620, and so on.

The interface 600 includes additional elements that may be selected to customize the visualization of the pleural surface and ultrasound volume. For example, the interface may include an add light source option 624, a topo display option 626, a volume render option 628, and a 2D slice option 630. Each option may be presented as a selectable user interface element that, when selected, launches display of a corresponding image/feature on the interface 600 and in some examples may also launch display of a window of options related to the function of the option. For example, selecting the add light source option 624 may open a light source menu similar to the light source menu 634. The light source menu 634 may include a title block 632 which displays the name of the virtual light source 620. The default name of the light source may be “light source” followed by a number individual to the light source. For example, the virtual light source 620 is labeled “light source 1” in the title block 632. If a second light source were added, the second light source may be labeled “light source 2”. The light source menu 634 may further include a brightness selector 610. The brightness selector 610 may in some cases be a sliding scale between 0% brightness and 100% brightness, where 100% brightness represents the maximum brightness of the artificial light source. The maximum brightness may be set such that the brightness of the light source does not exceed a brightness that would make details of the pleural surface less visible in to most users. 0% brightness may be used if the virtual light source gives off no light. A slider may be used to set the brightness of the virtual light source between 0% and 100% depending on the user preference. In some cases, a brightness level may be automatically selected to highlight features of the pleural surface. In some examples, the brightness selector 610 may be a text box that allows the user to type a desired brightness level, or another method to select the brightness of the virtual light source.

The light source menu 634 may further include hue boxes 612. The hue boxes 612 may allow the user to select what color light the virtual light source 620 emits. In some examples, particularly in examples where more than one virtual light sources are in use, the color of light emitted by a virtual light source may be used to identify where the light highlighting a feature of the pleural surface originates from. In some example, knowing the origin of light striking a figure may provide information to the user about the shape, size and location of a particular feature. In one example, the hue boxes 612 include a red box 636, a green box 638, and a blue box 640. In some example, a user may select one of the red box 636, the green box 638, and the blue box 640 to select if the virtual light source emits red, green or blue light. One or more boxes may be selected to form composite colors. For example, selecting the red box 636 and the blue box 640 may result in the virtual light source emitting violet light. Selecting the red box 636, the green box 638 and the blue box 640 may produce white light. In other examples, the red box 636, the green box 638, and the blue box 640 may be text boxes wherein a user can input numerical values that represent the color of light the user intends for the virtual light source to produce. These numerical values may correspond to the standard RGB color codes, where a number between 0 and 255 is input into each of the red box 636, the green box 638, and the blue box 640 to form a final light color. In this example, white light may be produced by inputting 255 into each of the red box 636, the green box 638, and the blue box 640.

The light source menu 634 may further include the coordinate selector 614. The coordinate selector 614 may display the x, y, and z coordinates of the light source with respect to the Cartesian coordinate system 690. In some examples, the position of the light source may be adjusted by clicking and dragging the virtual light source 620 within the 3D pleural surface image 404. In other examples, the desired coordinates of the virtual light source 620 may be input by the user into the coordinate selector 614. For example, the coordinate selector 614 may include the text labels "x=", "y=", and "z=" with a fillable field corresponding to each text label. The desired x, y, positions of the virtual light source may be typed by a user into the fillable field corresponding to each text label.

Figure 7:
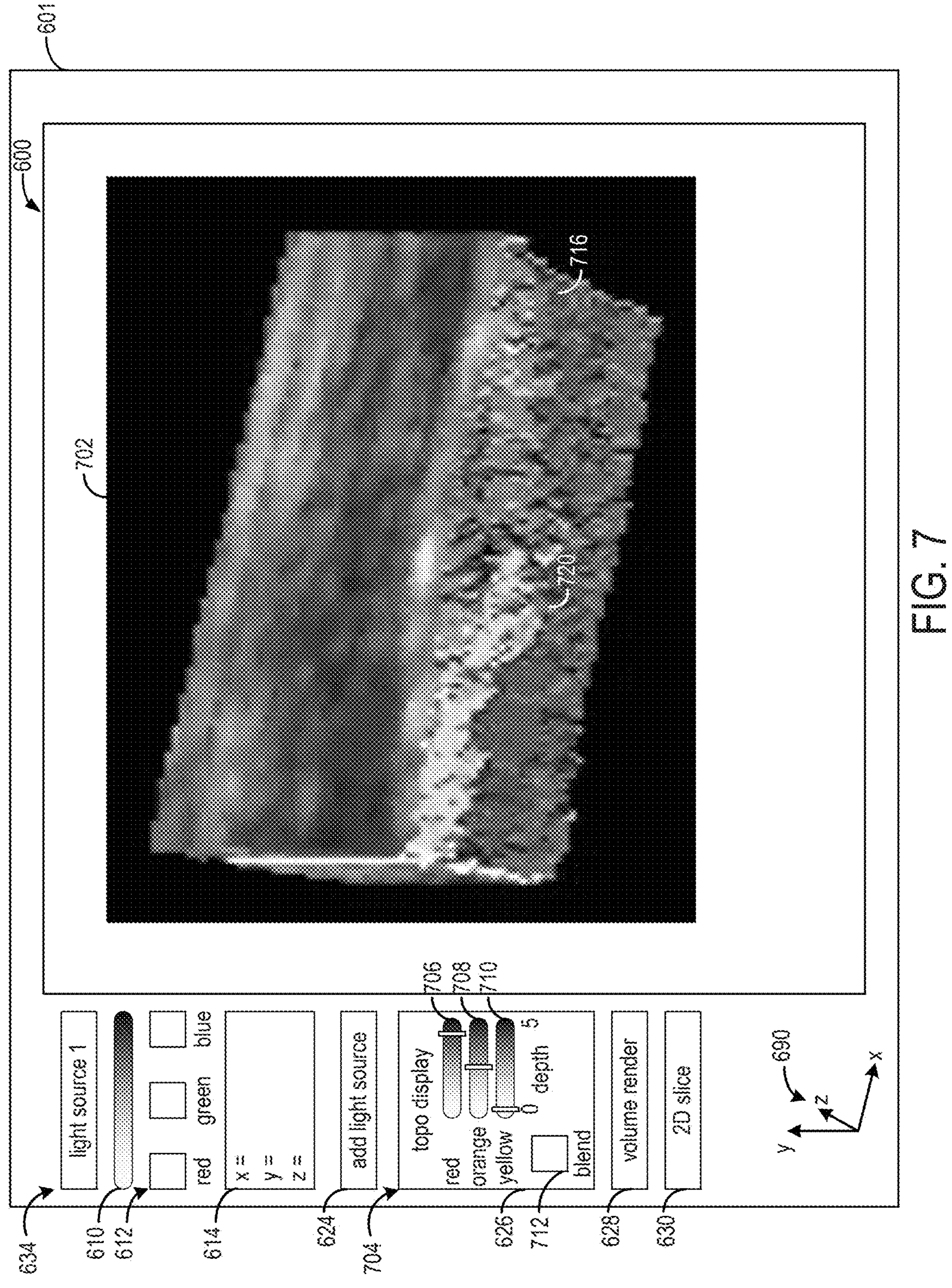
Figure 10:
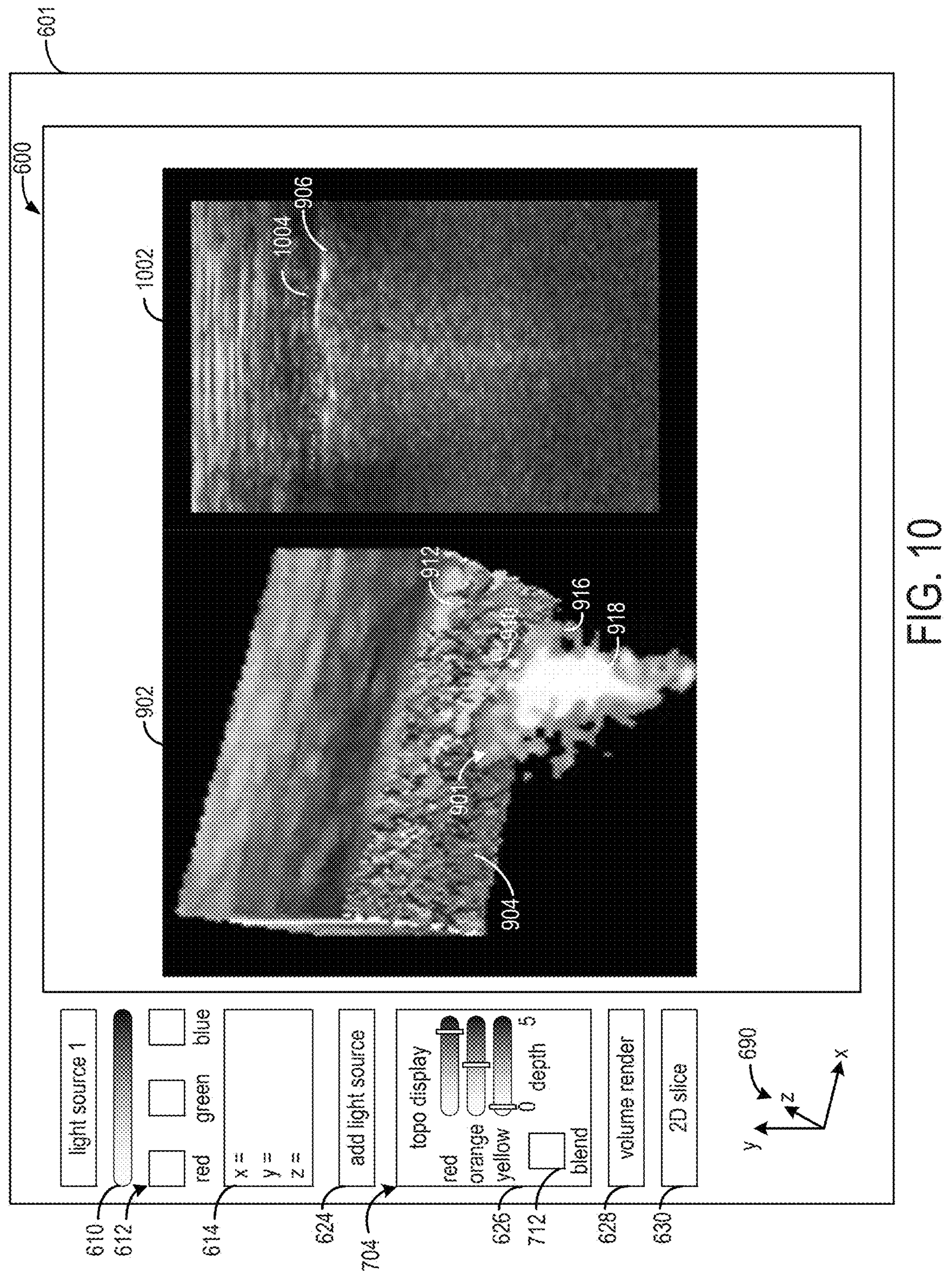

The topo display option 626 may be selected to display the topographic representation of the 3D pleural surface image, which is shown in FIG. 7. Further, selection of the topo display option 626 may result in display of a menu that allows the user to select and adjust features of the topographic representation, such as the depth ranges and colors associated with each depth range. The menu associated with the topo display option 626 is shown in FIG. 7. The volume render option 628 may be selected to display a volume rendering of the area below the pleural surface, as explained above with respect to FIG. 5. In some examples, selection of the volume render option 628 may result in display of a menu illustrating options related to the volume rendering, such as the color of the volume rendering. A volume rendered image is shown in FIGS. 9 and 10.

Figure 8:
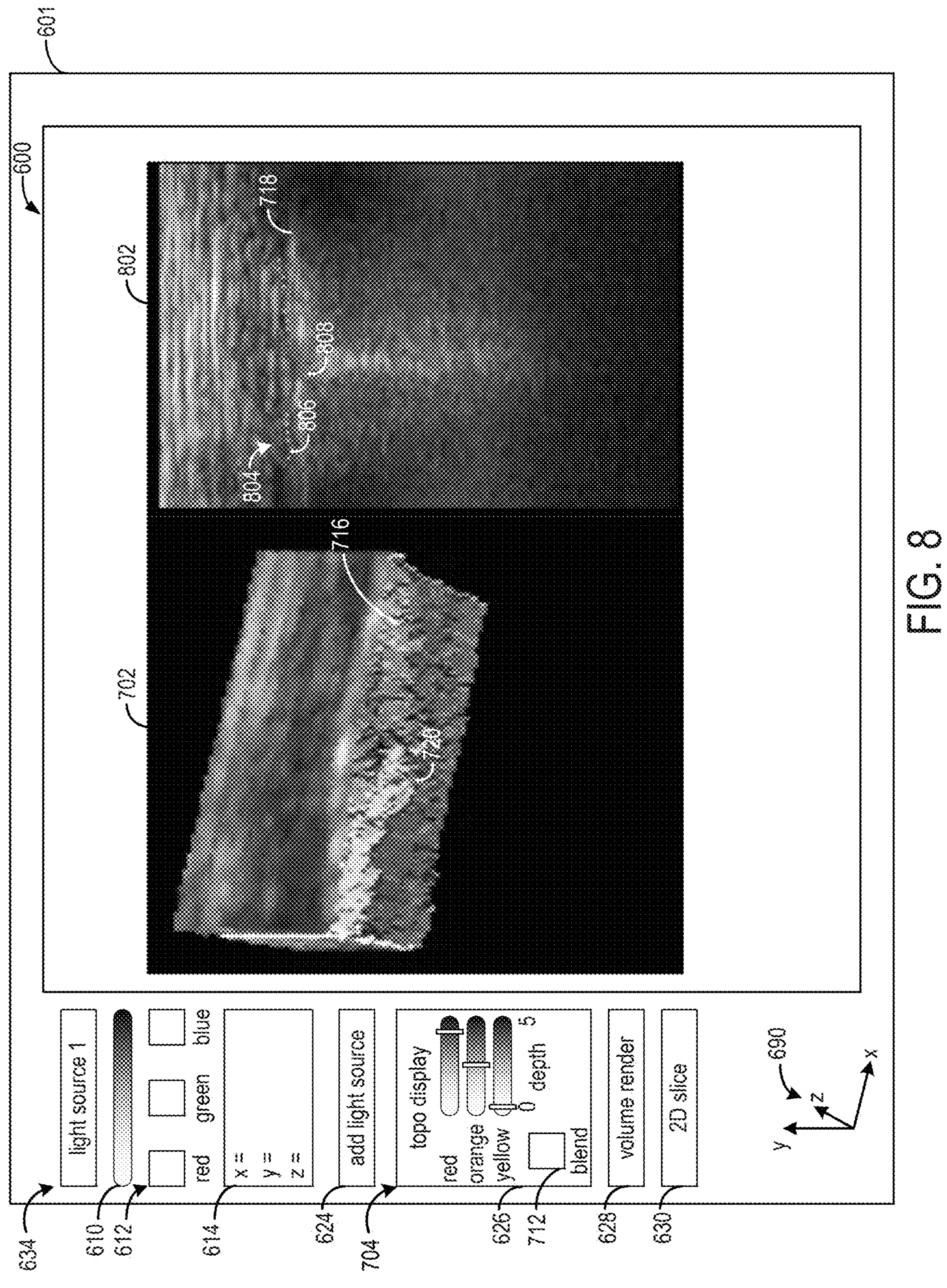

The 2D slice option 630 may be selected to display a selected 2D plane from the ultrasound volume. In some examples, selection of the 2D slice option 630 may result in display of a menu that allows the user to select a 2D slice to be displayed as the 2D plane. As explained previously, the 2D plane image that is displayed may be a 2D slice of the entire volume of ultrasound data (e.g., the 3D volume without the volume below the pleural surface removed). In this way, the displayed 2D plane may include a view of the area below the pleural surface, which in some cases may include artifacts such as B-lines. In some examples, a 2D slice of the depression or projection of the pleural surface that includes the most colored voxels or includes voxels of the greatest depth may be selected automatically to be displayed as the 2D plane. In other examples, the user may select the 2D plane by inputting vector coordinates of the desired plane, or by drawing a line across a portion of the 3D pleural surface image 404. In some examples, the user may select a feature of the 3D pleural surface image 404, and the interface may automatically select and display a 2D plane of the feature. Example 2D plane images are shown in FIGS. 8 and 10.

As shown in FIG. 7, selection of the topo display option 626 results in display of a topographic representation of the 3D pleural surface/3D pleural surface image, herein referred to as a topographic image 702. Further, selection of the topo display option 626 may result in display of a topographic menu 704 that includes elements for selecting/adjusting one or more adjustable features of topographic image 702. The topographic menu 704 includes one or more depth ranges, including a first depth range 706, a second depth range 708, and a third depth range 710. In some examples, each depth range may be represented by a slider; however, other configurations are possible. In some examples, each depth range may include a text field where a user can input an upper and lower threshold for each depth range. For example, the first depth range may be 0-1 mm, the second depth range may be 1-3 mm, and the third depth range may be all depths greater than 3 mm. It is to be appreciated that each depth range may encompass a range of values of orthogonal deviation from an expected pleural line, with positive values indicating deviation in the negative y direction of the coordinate system 690.

In the example topographic menu 704 shown in FIG. 7, the depth ranges are configured as positive depths representing protrusions, however, other topographic menus may include depth ranges that may include negative depths to include depressions as well as protrusions. The third depth range 710 may include a slider that can be adjusted to select the lower depth threshold for the third depth range 710. The third depth range 710 may be labeled with the color yellow to indicate that voxels within the third depth range 710 may be colored yellow in the topographic image 702. Voxels that have a depth less than the lower threshold of the third depth range 710 may be rendered in black and white/grayscale, and be considered within the normal range of depth variation for the pleural surface. The second depth range 708 may include a slider that can be adjusted to select the lower depth threshold for the second depth range 708. The lower depth threshold for the second depth range 708 may also serve as the upper threshold for the third depth range 710. The second depth range 708 may be labeled with the color orange to indicate that voxels within the second depth range 708 may be colored orange in the topographic image 702. The first depth range 706 may include a slider that can be adjusted to select the lower depth threshold for the first depth range 706. The lower depth threshold for the first depth range 706 may also serve as the upper threshold for the second depth range 708. The first depth range 706 may not have an upper threshold and may encompass all depths greater than the lower depth threshold for the first depth range 706. The first depth range 706 may be labeled with the color red to indicate that voxels within the first depth range 706 may be colored red in the topographic image 702. In some examples, more or fewer than three depth ranges may be included.

As explained above, in some examples, the topographic menu 704 may include options for setting negative depth ranges in addition to positive depth ranges, with a central depth range defining the normal range of depth variation for the pleural surface, one or more depth ranges that define depth ranges for protrusions of the pleural surface, and one or more depth ranges that define depressions in the pleural surface. In some examples, protrusions may be colored in yellow, orange, and red and depressions may be colored in green, blue and purple. In some examples, a user may add or delete depth ranges to customize the number of depth ranges and the colors associated with each depth range. In some examples, the depth ranges depicted in the topographic menu 704 may be automatically selected depending on the demographics of the patient. For example, in adult patients, protrusions at a depth greater than 5 mm are considered severe, so the third depth range 710 may include voxels at a depth greater than 5 mm. In a child, protrusions at a depth greater than 2 mm are considered severe, so the third depth range 710 may include voxels at a depth greater than 2 mm when the imaged patient is a child.

The topographic menu 704 may further include a blend option 712. The blend option may allow a user to control the opacity of the color applied to the grayscale voxels within the topographic image 702. In some examples, via the blend option 712, the user may be able to type or select an opacity value between 0% and 100%, where an opacity of 0% applies no color to the topographic image 702 and an opacity of 100% replaces the grayscale values of each individual colored voxel with the color assigned to each voxel based on the depth range the voxel is sorted into. The topographic image may be initially displayed with color at a default opacity value, such as 20%, that allows the colors associated with each depth range as well as the grayscale value of each voxel to be visible, but the opacity may be adjusted by the user.

The user interface 600 may include the topographic image 702. The topographic image 702 may include a pleural surface 716. The pleural surface 716 may be shown in a perspective view (e.g., according to the coordinate system 690, which may depict the coordinates of the 3D pleural surface volume depicted in the topographic image 702) with the pleural surface 716 forming the bottom of the 3D pleural surface volume. The pleural surface may be the bottom of the pleural line. In the perspective view, the pleural line may be a pleural plane that extends in an x-z plane and the depth of each pixel of the pleural surface 716 may be a deviation along the y axis from the x-z plane that defines the pleural line. In the example topographic image 702 shown in FIG. 7, a bulge 720 may be visible on the pleural surface 716. The perspective view and lighting of the pleural surface 716 may make bulges such as the bulge 720 more visible. The bulge 720 may be comprised of a plurality of voxels/pixels that fall within the first depth range 706, the second depth range 708, and the third depth range 710 (each pixel of the pleural surface 716 may represent a voxel of the ultrasound volume). Pixels (representing voxels) within the bulge 720 belonging to the first depth range 706 may be colored yellow, pixels within the bulge 720 belonging to the second depth range 708 may be colored orange, and pixels within the bulge 720 belonging to the third depth range 710 may be colored red. Pixels that are in grayscale may be considered normal depth (e.g. within a threshold of the baseline depth of the pleural surface/expected pleural line). Coloring only pixels with depths outside the normal depth range may make features such as the bulge 720 easy for a user to identify, particularly as the features move during patient breathing (e.g., during 4D imaging). Color coding the pleural surface by depth may help a user understand the shape and size of various protrusions/depressions. In some examples, more than one bulge and/or depression may be identified in the pleural surface 716.

FIG. 8 shows the topographic image 702 displayed alongside a 2D image 802 that depicts a selected 2D plane of the entire volume of ultrasound data, wherein the 2D image 802 is displayed in response to user selection of the 2D slice option 630. The selected 2D plane depicted in 2D image 802 may be in the x-y plane and taken along a default, user-specified, or automatically-selected point along the z axis. Because the 2D image 802 depicts a 2D plane selected from the entire volume of ultrasound data with all pixels for the 2D image (representing voxels of one slice of the 3D volume) having zero transparency, features below the pleural surface are depicted in addition to the pleural line.

The 2D image 802 may be annotated to visually depict pleural irregularities and/or the relative depth of the pleural surface. For example, in FIG. 8, a plurality of dots 804 is arranged a small distance above the pleural line 718 (e.g., a few pixels above the pleural line). Each dot may be colored based on the relative depth/orthogonal deviation of the pleural surface directly below that dot in a manner similar to the topographic coloring of the pleural surface of the topographic image. For example, green dots, such as first dot 806, may indicate the pleural surface directly below the dot is within a normal depth/deviation range (e.g., within 1 mm of the baseline depth) while red dots, such as second dot 808, may indicate the pleural surface directly below the dot is not within the normal depth/deviation range. In some examples, the plurality of dots 804 may be toggled on or off in a menu that may be opened when the 2D slice option 630 is selected.

When 4D imaging is being carried out, a new 2D plane may be selected and displayed for each new volume of ultrasound data that is acquired, such that both the topographic image 702 and the 2D image 802 are updated at a framerate corresponding to the rate of volume acquisition. The topographic coloring of the topographic image 702 and the plurality of dots on the 2D image 802 may be updated in real time, as each new volume is acquired. In examples where the 2D plane that is imaged in 2D image 802 is automatically selected to be the plane that depicts the most depth deviation, the selected 2D plane may be change (e.g., in position along the z axis) from volume to volume, at least in some examples.

FIG. 9 shows a topographic image 902 similar to the topographic image 702; however, both the topographic image 702 and the topographic image 902 are images generated from live volumetric imaging (e.g., wherein multiple volumes are acquired over time) and the topographic image 902 is generated from a subsequent volume acquired after the volume from which the topographic image 702 was generated. Further, responsive to selection of the volume render option 628, the topographic image 902 includes a volume rendering 901 of the area below the pleura. The topographic image 902 may include a pleural surface 904 and the volume rendering 901 is included in the topographic image 902 in the area below the pleural surface 904. The coloring of the pleural surface 904 based on depth results in visualization of at least a first bulge 910 and a second bulge 912 in the pleural surface 904.

As appreciated by FIG. 9, the volume rendering 901 may not span the entire area under the pleural surface 904 but may instead include only a rendering of an anatomical feature of interest, such as a consolidation. To accomplish this, the transparency of the voxels below the pleural surface may be set to be semi-transparent while the voxels of the pleural surface may be set to have no transparency. In doing so, only voxels with a brightness over a first brightness threshold may be rendered or shaded, or only pixels that result from the volume rendering have a brightness over a threshold may be displayed. Further, the shading/coloring may be performed with multiple colors. For example, pixels within a first brightness range may be displayed in purple, as shown in the purple regions 916 of the volume rendering 901. Pixels within the second brightness range may be displayed in white, as shown in the white regions 918 of the volume rendering 901. The colors of the pixels of the volume rendering 901 may be selected so that they are different from the colors used to generate the topographic representation of the pleural surface 904. It is to be appreciated that the pleural surface 904 is rendered as an opaque or solid surface while at least some of the ultrasound data below the pleural surface 904 is suppressed, such as using transparency. In some examples, the pixels below the pleural surface 904 may be made transparent other than the pixels of the volume rendering 901, which may be opaque or semi-transparent. In some examples, the 3D pleural surface volume may be rendered for display (e.g., as the topographic image 902) using volume rendering to allow both the pleural surface and features within the volume below the pleural surface to be visualized.

A menu accessible by selecting the volume render option 628 may allow a user to adjust settings of the volume rendering procedure. In some examples, a user may be able to adjust the colorization of the volume rendering, such as the number of brightness ranges as well as the range of brightness included within each brightness range. The user may also be able to change the colors associated with each brightness range, as well as the opacity of the color applied to each pixel within each brightness range.

FIG. 10 includes the topographic image 902 (including the volume rendering 901) displayed adjacent to a 2D image 1002. Similar to the 2D image 802, the 2D image 1002 depicts a selected 2D plane of the entire volume of ultrasound data. The selected 2D plane depicted in 2D image 1002 may be in the x-y plane and taken along a default, user-specified, or automatically-selected point along the z axis. Because the 2D image 1002 depicts the entire volume of ultrasound data, features below the pleural surface are depicted in addition to the pleural line. 2D image 1002 includes a plurality of dots 1004 arranged a small distance above the pleural line 906 (e.g., a few pixels above the pleural line). Each dot may be colored based on the relative depth of the pleural surface directly below that dot in a manner similar to the topographic coloring of the pleural surface of the topographic image 902. For example, green dots may indicate the pleural surface directly below the dot is within a normal depth range (e.g., within 1 mm of the baseline depth) while red dots may indicate the pleural surface directly below the dot is not within the normal depth range. Additionally, it is to be appreciated that the feature visualized in the volume rendering 901 is also visible in the 2D image (e.g., as the bright streak under the pleural line 906).

In this way, a processor may automatically generate a 3D pleural surface of a lung pleura viewed from an inside of a lung and looking outward based on ultrasound imaging signals and may automatically color the pleural surface based on relative depth/deviation from an expected pleural line. The methods and systems described herein enable visualization of an entire pleural surface which is captured by an ultrasound probe, as opposed to a representative 2D image which may or may not include pathologies present and/or extending into 3D space. This may eliminate a diagnostic step of searching for specific views of the pleural surface. Further, the topographic representation, wherein the pleural surface is colored based on relative depth, may enhance visualization of certain anatomical features of interest to thereby aid in clinical diagnoses, but without having to undertake computationally expensive operations typically associated with providing actual clinical diagnoses. In this way, a wide range of ultrasound findings and pathologies may be visualized, including pleural irregularities, pneumothorax, and viral and bacterial infections. As a result, an amount of time the healthcare professional spends reviewing the medical images may be reduced, enabling the healthcare professional to focus on patient care and comfort. Further, by including the 3D pleural surface with a volume rendering of underlying anatomical features (e.g., below the pleural surface), the pleural irregularities may be displayed in an anatomically relevant environment in order to further simplify a diagnostic process.

As disclosed herein, a 3D volume of ultrasound data of a lung of a patient is obtained. The pleural line is first identified in the 3D volume. This is performed on all the images (or slices) that constitute the 3D volume. A typical 3D ultrasound volume has about 100-200 frames or slices. The pleural line is identified in each slice by an image processing algorithm as described above, e.g., an edge detection algorithm that combines pixel values and gradients to detect the pleural line. Once the pleural line in all slices of the 3D volume are identified, the pleural surface is generated as a 3D mesh that links together all pleural lines from all slices. The voxels along the pleural surface are assigned 100% opacity (0 transparency), so when being volume rendered from inside-out appear as a solid surface. In addition, these voxels along the pleural surface are assigned topographic color based on the relative orthogonal depth deviation from the expected pleural line/surface. The voxels below the pleural line are partially removed, or suppressed, by being assigned higher transparency values. The 3D volume (after adjusting the transparency of the voxels of the pleural surface and below the pleural surface, as explained above, and further after assigning the topographic color to the voxels of the pleural surface based on depth) is then volume rendered to generate one or more images from a desired perspective. The volume rendering may be performed from a view angle so as to create a view of the pleural surface from inside of the lung looking outward. This process (e.g., first detecting the pleural surface in the 3D volume and then assigning higher transparency values to the voxels below the pleural surface and zero transparency to the voxels of the pleural surface) may reduce the processing power and time for volume rendering, which may enable real-time volume rendering for live/4D imaging.

Once the pleural surface in the 3D volume is detected and then higher transparency values are assigned to the voxels below the pleural surface, the full opacity pleural surface voxels (e.g., the voxels that form the pleural surface and are assigned 100% opacity) may be rendered for display in a variety of ways. For example, the pleural surface voxels may be assigned a uniform brightness that is color modulated based on the calculated deviation from the baseline/expected pleural surface. As another example, the pleural surface voxels may be assigned the original brightness of the 2D pixels in addition to the color modulation (e.g., the blending as described above). As a still further example, a uniform gray level may be assigned to each pleural surface voxel that is then modulated based on shading (e.g., by placing a virtual light source, as explained above), which will usually give a good hint about the underlying 3D shape (and in some examples, initial smoothing may be performed), with or without the color modulation. In some examples, additionally or alternatively, a threshold of topographic deviation may be utilized. For pleural surface voxels having a depth deviation below the threshold, the displayed values are presented in grayscale based on depth deviation. For pleural surface voxels above the threshold, the display is colorized based on the depth deviation. In addition, shading is used to further emphasize the 3D effect.

A technical effect of generating a 3D pleural surface of a lung pleura viewed from an inside of a lung and looking outward with the pleural surface colored based on relative depth is that a processing power used by an imaging system may be reduced due to a reduced number of additional imaging scans as a result of increased accuracy and detail of pleural surface image renderings and may be reduced relative to traditional forms of computer-aided diagnosis tools.

The disclosure also provides support for a method for imaging a lung of a patient, comprising: identifying, within a three-dimensional (3D) volume of ultrasound data of the lung of the patient, a pleural surface of a pleural line, identifying an orthogonal deviation of each voxel of the pleural surface relative to an expected pleural line, and outputting an image rendered from the 3D volume, the image including a plurality of pixels colored based on the orthogonal deviation of each voxel of the pleural surface and depicting the pleural surface as if viewed from an inside of the lung and looking outward. In a first example of the method, the method further comprises: positioning a virtual light source to shade the pleural surface, wherein the virtual light source is positioned as if inside the lung and looking outward. In a second example of the method, optionally including the first example, coloring the plurality of pixels based on the orthogonal deviation comprises: assigning a first color to pixels representing voxels having orthogonal deviations within a first range relative to the expected pleural line, and assigning a second color to pixels representing voxels having orthogonal deviations within a second range relative to the expected pleural line, the second range different than the first range. In a third example of the method, optionally including one or both of the first and second examples, the method further comprises: assigning a first transparency value to voxels of the pleural surface and assigning a second transparency value to voxels below the pleural surface, the second transparency value higher than the first transparency value to form an adjusted-transparency 3D volume, and volume rendering the adjusted-transparency 3D volume to form the image. In a fourth example of the method, optionally including one or more or each of the first through third examples, the first transparency value is 0. In a fifth example of the method, optionally including one or more or each of the first through fourth examples, the method further comprises: selecting a two-dimensional (2D) plane from the 3D volume, and displaying a 2D image of the 2D plane adjacent to the image. In a sixth example of the method, optionally including one or more or each of the first through fifth examples, the method further comprises: displaying a plurality of dots above a pleural line in the 2D image, wherein each dot is colored based on a depth of the pleural surface directly below that dot. In a seventh example of the method, optionally including one or more or each of the first through sixth examples, the 3D volume of ultrasound data is a first 3D volume of ultrasound data and the image is a first image, wherein outputting the first image comprises outputting the first image for display on a display device while a second 3D volume of ultrasound data is being acquired, and further comprising outputting a second image rendered from the second 3D volume, the second image including a second plurality of pixels colored based on an orthogonal deviation of each voxel of a pleural surface in the second 3D volume.

The disclosure also provides support for a system, comprising: a display device, and a processor configured with instructions in non-transitory memory that, when executed, cause the processor to: generate a three-dimensional (3D) pleural surface volume including a pleural surface of a lung from a volume of ultrasound data, wherein each voxel of the pleural surface in the 3D pleural surface volume is colored based on an orthogonal deviation of that voxel relative to an expected pleural line and has a transparency value of 0, and output an image rendered from the 3D pleural surface volume for display on the display device. In a first example of the system, generating the 3D pleural surface volume comprises: detecting a bottom edge of a pleural line in the volume of ultrasound data, the bottom edge forming the pleural surface, setting the transparency value of each voxel of the pleural surface to 0, determining the orthogonal deviation each voxel of the pleural surface relative to the expected pleural line, assigning a respective color value to each voxel of the plural surface based on the corresponding orthogonal deviation for that voxel, and setting a respective transparency value for each voxel below the bottom edge of the pleural line to a value greater than 0. In a second example of the system, optionally including the first example, assigning a respective color value to each voxel of the plural surface based on the corresponding orthogonal deviation for that voxel comprises: assigning a first color to voxels having orthogonal deviations within a first range relative to the expected pleural line, and assigning a second color to voxels having orthogonal deviations within a second range relative to the expected pleural line, the second range different than the first range. In a third example of the system, optionally including one or both of the first and second examples, the system further comprises: for each voxel assigned a color, blending that color with an underlying grayscale value, the underlying grayscale value representing an echogenicity of that voxel. In a fourth example of the system, optionally including one or more or each of the first through third examples, outputting the image rendered from the 3D pleural surface volume for display on the display device comprises volume rendering the 3D pleural surface volume to form the image, such that the image includes the pleural surface as if viewed from an inside of the lung and looking outward and pixels of the pleural surface are colored corresponding to coloring of voxels of the pleural surface. In a fifth example of the system, optionally including one or more or each of the first through fourth examples, the processor is configured with further instructions that, when executed, cause the processor to: select a two-dimensional (2D) plane from the volume of ultrasound data, and output a 2D image of the 2D plane adjacent to the image rendered from the 3D pleural surface volume for display on the display device. In a sixth example of the system, optionally including one or more or each of the first through fifth examples, the 2D image includes a plurality of dots above a pleural line in the 2D image, wherein each dot is colored based on a depth of the pleural surface directly below that dot. In a seventh example of the system, optionally including one or more or each of the first through sixth examples, the 2D plane is selected automatically based on a degree of orthogonal deviation of the pleural surface in that 2D plane.

The disclosure also provides support for a method, comprising: acquiring volumetric ultrasound data of a lung of a patient over time, generating a first topographic image from a first volume of the volumetric ultrasound data, the first topographic image depicting a pleural surface viewed from an inside of the lung and looking outward with one or more pixels of the pleural surface colored based on an orthogonal deviation of the pleural surface from an expected pleural line, displaying the first topographic image while the volumetric ultrasound data continues to be acquired, generating a second topographic image from a second volume of the volumetric ultrasound data, the second topographic image depicting the pleural surface viewed from the inside of the lung and looking outward with one or more pixels of the pleural surface colored based on the orthogonal deviation of the pleural surface from the expected pleural line, and displaying the second topographic image. In a first example of the method, generating the first topographic image includes partially removing ultrasound data on a side of the pleural surface towards the inside of the lung using transparency. In a second example of the method, optionally including the first example, partially removing ultrasound data on the side of the pleural surface using transparency includes adjusting transparency of the first topographic image such that one or more features on the side of the pleural surface are semi-transparent while the pleural surface is rendered as an opaque or solid surface. In a third example of the method, optionally including one or both of the first and second examples, displaying the first topographic image comprises displaying the first topographic image alongside a 2D image of a selected 2D plane of the first volume.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A method for imaging a lung of a patient, comprising:

identifying, within a three-dimensional (3D) volume of ultrasound data of the lung of the patient, a pleural surface of a pleural line;

identifying an orthogonal deviation of each voxel of the pleural surface relative to an expected pleural line; and outputting an image rendered from the 3D volume, the image including a plurality of pixels colored based on the orthogonal deviation of each voxel of the pleural surface and depicting the pleural surface as if viewed from an inside of the lung and looking outward.

2. The method of claim 1, further comprising positioning a virtual light source to shade the pleural surface, wherein the virtual light source is positioned as if inside the lung and looking outward.

3. The method of claim 1, wherein coloring the plurality of pixels based on the orthogonal deviation comprises:

assigning a first color to pixels representing voxels having orthogonal deviations within a first range relative to the expected pleural line; and assigning a second color to pixels representing voxels having orthogonal deviations within a second range relative to the expected pleural line, the second range different than the first range.

4. The method of claim 1, further comprising:

assigning a first transparency value to voxels of the pleural surface and assigning a second transparency value to voxels below the pleural surface, the second transparency value higher than the first transparency value to form an adjusted-transparency 3D volume; and volume rendering the adjusted-transparency 3D volume to form the image.

5. The method of claim 4, wherein the first transparency value is 0.

6. The method of claim 1, further comprising:

selecting a two-dimensional (2D) plane from the 3D volume; and displaying a 2D image of the 2D plane adjacent to the image.

7. The method of claim 6, further comprising displaying a plurality of dots above a pleural line in the 2D image, wherein each dot is colored based on a depth of the pleural surface directly below that dot.

8. The method of claim 1, wherein the 3D volume of ultrasound data is a first 3D volume of ultrasound data and the image is a first image, wherein outputting the first image comprises outputting the first image for display on a display device while a second 3D volume of ultrasound data is being acquired, and further comprising outputting a second image rendered from the second 3D volume, the second image including a second plurality of pixels colored based on an orthogonal deviation of each voxel of a pleural surface in the second 3D volume.

9. A system, comprising:

a display device; and a processor configured with instructions in non-transitory memory that, when executed, cause the processor to:

generate a three-dimensional (3D) pleural surface volume including a pleural surface of a lung from a volume of ultrasound data, wherein each voxel of the pleural surface in the 3D pleural surface volume is colored based on an orthogonal deviation of that voxel relative to an expected pleural line and has a transparency value of 0; and output an image rendered from the 3D pleural surface volume for display on the display device.

10. The system of claim 9, wherein generating the 3D pleural surface volume comprises:

detecting a bottom edge of a pleural line in the volume of ultrasound data, the bottom edge forming the pleural surface;

setting the transparency value of each voxel of the pleural surface to 0;

determining the orthogonal deviation each voxel of the pleural surface relative to the expected pleural line;

assigning a respective color value to each voxel of the plural surface based on the corresponding orthogonal deviation for that voxel; and setting a respective transparency value for each voxel below the bottom edge of the pleural line to a value greater than 0.

11. The system of claim 10, wherein assigning a respective color value to each voxel of the plural surface based on the corresponding orthogonal deviation for that voxel comprises:

assigning a first color to voxels having orthogonal deviations within a first range relative to the expected pleural line; and assigning a second color to voxels having orthogonal deviations within a second range relative to the expected pleural line, the second range different than the first range.

12. The system of claim 11, further comprising, for each voxel assigned a color, blending that color with an underlying grayscale value, the underlying grayscale value representing an echogenicity of that voxel.

13. The system of claim 9, wherein outputting the image rendered from the 3D pleural surface volume for display on the display device comprises volume rendering the 3D pleural surface volume to form the image, such that the image includes the pleural surface as if viewed from an inside of the lung and looking outward and pixels of the pleural surface are colored corresponding to coloring of voxels of the pleural surface.

14. The system of claim 9, wherein the processor is configured with further instructions that, when executed, cause the processor to:

select a two-dimensional (2D) plane from the volume of ultrasound data; and output a 2D image of the 2D plane adjacent to the image rendered from the 3D pleural surface volume for display on the display device.

15. The system of claim 14, wherein the 2D image includes a plurality of dots above a pleural line in the 2D image, wherein each dot is colored based on a depth of the pleural surface directly below that dot.

16. The system of claim 15, wherein the 2D plane is selected automatically based on a degree of orthogonal deviation of the pleural surface in that 2D plane.

17. A method, comprising:

acquiring volumetric ultrasound data of a lung of a patient over time;

generating a first topographic image from a first volume of the volumetric ultrasound data, the first topographic image depicting a pleural surface viewed from an inside of the lung and looking outward with one or more pixels of the pleural surface colored based on an orthogonal deviation of the pleural surface from an expected pleural line;

displaying the first topographic image while the volumetric ultrasound data continues to be acquired;

generating a second topographic image from a second volume of the volumetric ultrasound data, the second topographic image depicting the pleural surface viewed from the inside of the lung and looking outward with one or more pixels of the pleural surface colored based on the orthogonal deviation of the pleural surface from the expected pleural line; and displaying the second topographic image.

18. The method of claim 17, wherein generating the first topographic image includes partially removing ultrasound data on a side of the pleural surface towards the inside of the lung using transparency.

19. The method of claim 18, wherein partially removing ultrasound data on the side of the pleural surface using transparency includes adjusting transparency of the first topographic image such that one or more features on the side of the pleural surface are semi-transparent while the pleural surface is rendered as an opaque or solid surface.

20. The method of claim 17, wherein displaying the first topographic image comprises displaying the first topographic image alongside a 2D image of a selected 2D plane of the first volume.

* * * * *